United States Patent [19]

Bellucci et al.

[11] Patent Number: 4,851,031
[45] Date of Patent: Jul. 25, 1989

[54] USE OF QUINOLINE DERIVATIVES FOR PROTECTING CULTIVATED PLANTS

[75] Inventors: Sergio Bellucci, Wallbach; Adolf Hubele; Andreas Nyffeler, both of Magden, all of Switzerland

[73] Assignee: Ciba-Geigy Corporation, Ardsley, N.Y.

[21] Appl. No.: 906,347

[22] Filed: Sep. 10, 1986

Related U.S. Application Data

[63] Continuation-in-part of Ser. No. 710,252, Mar. 11, 1985, abandoned.

[30] Foreign Application Priority Data

Mar. 15, 1984 [CH] Switzerland .................. 1291/84

[51] Int. Cl.⁴ ...................... A01N 43/50; A01N 43/42
[52] U.S. Cl. ........................... 71/92; 71/90; 71/94
[58] Field of Search ..................... 71/92, 94

[56] References Cited

U.S. PATENT DOCUMENTS

| | | | |
|---|---|---|---|
| 3,133,810 | 5/1964 | Hamm | 71/118 |
| 4,188,487 | 11/1980 | Los | 548/301 |
| 4,602,932 | 7/1986 | Handte et al. | 71/94 |
| 4,623,727 | 11/1986 | Hubele II | 71/92 |

FOREIGN PATENT DOCUMENTS

| | | | |
|---|---|---|---|
| A041623 | 12/1981 | European Pat. Off. | 71/92 |
| A094349 | 11/1983 | European Pat. Off. | 71/94 |
| 2546845 | 4/1977 | Fed. Rep. of Germany | 71/94 |

OTHER PUBLICATIONS

Pesticide Manual, 8th Ed., p. 473 & EP 41623, title page and pp. 191, 192, 269 and 229.
Pesticide Manual, 8th ed., p. 474 & EP 41623, title page and pp. 191, 192, 219 and 259.

Primary Examiner—Glennon H. Hollrah
Assistant Examiner—S. Treanor
Attorney, Agent, or Firm—Edward McC. Roberts

[57] ABSTRACT

The invention relates to the use of quinoline derivatives of formula

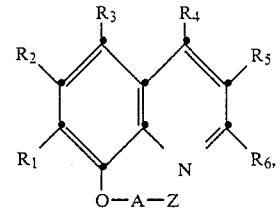

wherein
$R_1$, $R_2$ and $R_3$ are each independently hydrogen, halogen, nitro, cyano, $C_1$–$C_4$alkyl or $C_1$–$C_3$alkoxy,
$R_4$, $R_5$ and $R_6$ are each independently hydrogen, halogen or $C_1$–$C_3$alkyl,
A is a group selected from —$CH_2$—, —$CH_2$—$CH_2$— or —$CH(CH_3)$— and
Z is (a) cyano or amidoxime which may be acylated at the oxygen atom, or (b) a carboxyl group or a salt thereof, a mercaptocarbonyl group or a salt thereof, an esterified carboxyl group, a thiocarbonyl group, an unsubstituted or a substituted carbamoyl group, a cyclized unsubstituted or substituted derivative of a carbamoyl group, or is a carbonohydrazido group; or A and Z together are an unsubstituted or a substituted tetrafuran-2-one ring.

and the acid addition salts and metal complexes thereof, for protecting cultivated plants from the harmful effects of herbicidally active derivatives of (4,5-dihydro-4-oxo-1H-imidaszol-2-yl)benzoic acid, (4,5-dihydro-4-oxo-1H-imidazo-1-2-yl)nicotinic acid and (4,5-dihydro-4-oxo-1H-imidazol-2-yl)quinolinecarboxylic acid.

The above mentioned herbicidal derivatives have the formula II

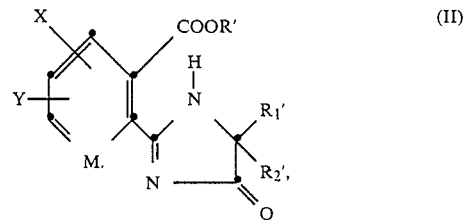

wherein R' is hydrogen, $C_1$–$C_4$alkyl, the ammonium cation or an organic ammonium cation, $R_1'$ is $C_1$–$C_4$alkyl, $R_2'$ is $C_1$–$C_4$alkyl or $C_3$–$C_6$cycloalkyl, or $R_1'$ and $R_2'$ together are $C_4$alkylene or $C_5$alkylene, M is the structural unit =CH— or =N—, X and Y are each independently of the other hydrogen, $C_1$–$C_4$alkyl or halogen or, if M is =N—, are additionally the structural unit —C($X_1$)=C($X_2$)— C($X_3$)=C($X_4$)—, wherein $X_1$, $X_2$, $X_3$ and $X_4$ are hydrogen or one or two of $X_1$, $X_2$, $X_3$ and $X_4$ are $C_1$–$C_4$alkyl and the others are hydrogen.

26 Claims, No Drawings

USE OF QUINOLINE DERIVATIVES FOR PROTECTING CULTIVATED PLANTS

This is a continuation-in-part of our application, Ser. No. 710,252, filed Mar. 11, 1985 now abandoned.

The present invention relates to the use of quinoline derivatives for protecting cultivated plants from the harmful effects of herbicidal derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2-yl)quinolinecarboxylic acid.

When applying herbicides such as the imidazole derivatives referred to above, appreciable damage may be caused to the cultivated plants depending on such factors as, for example, the concentration of herbicide, the mode of application, the species of cultivated plant, the nature of the soil, and climatic conditions such as the duration of exposure to light, temperature and rainfall. In particular, severe injury may result when, in the course of crop rotation, other cultivated plants that have no or only insufficient resistance to the herbicides are grown after the cultivated plants that are resistant to the herbicides.

It is known from published European patent specifications Nos. 86 750 and 94 349 that quinoline derivatives can be used for protecting cultivated plants from the harmful effects of aggressive agrochemicals.

Surprisingly, it has not been found that protection of cultivated plants from injury caused by herbicidal derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2yl)quinoline carboxylic acid can be afforded by dressing the seeds of said plants with a safener selected from the group of quinoline derivatives. The cited herbicides, which remain active in the soil for some considerable time, are preferably used in soybean crops, as soybean plants are sufficiently resistant to these herbicides. However, considerable injury is often caused to subsequent crops. This applies in particular to crops of cereals. By dressing the seeds of non-resistant cultivated plants it is possible to alternate soybean crops with crops of other cultivated plants without damage being caused by the herbicides to these subsequent crops. No loss of herbicidal activity against weeds and grasses results.

Furthermore, the use of quinoline derivatives also makes possible the direct application of the herbicidal derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2-yl)quinolinecarboxylic acid in crops of cultivated plants that have no or only insufficient resistance to these herbicides.

Quinoline derivatives suitable for protecting cultivated plants from the harmful effects of herbicidal derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2-yl)quinolinecarboxylic acid correspond to formula I

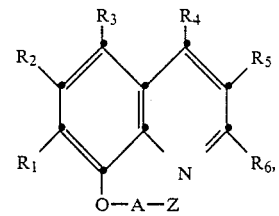

wherein $R_1$, $R_2$ and $R_3$ are each independently hydrogen, halogen, nitro, cyano, $C_1$-$C_4$alkyl or $C_1$-$C_3$alkoxy, $R_4$, $R_5$ and $R_6$ are each independently hydrogen, halogen or $C_1$-$C_3$alkyl, A is a group selected from —$CH_2$—, —$CH_2$—$CH_2$— or —$CH(CH_3)$— and Z is (a) cyano or amidoxime which may be acylated at the oxyen atom, or (b) a carboxyl group or a salt thereof, a mercaptocarbonyl group or a salt thereof, an esterified carboxyl group, a thiocarbonyl group, an unsubstituted or a substituted carbamoyl group, a cyclised unsubstituted or substituted derivative of a carbamoyl group, or is a carbonohydrazido group; or A and Z together are an unsubstituted or substituted tetrafuran-2-one ring, and the acid addition salts and metal complexes thereof.

By amidoxime group is meant the

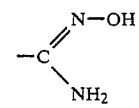

group. The amidoxime group can be acylated at the oxygen atom. Suitable amidoxime groups are those of the formula

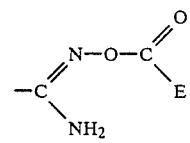

wherein

E is —$R_7$, —$OR_8$, —$SR_9$ or —$NR_{10}R_{11}$, where $R_7$ is $C_1$-$C_7$alkyl which is unsubstituted or substituted by halogen or $C_1$-$C_4$alkoxy, or is $C_3$-$C_6$cycloalkyl, $C_2$-$C_4$alkenyl, phenyl or phenyl which is substituted by halogen, nitro or $C_1$-$C_3$alkyl, benzyl or benzyl which is substituted by halogen, nitro or $C_1$-$C_3$alkyl, or is a 5- or 6-membered heterocyclic ring system which contains one or two hetero atoms selected from the group consisting of N, O or S, and which is unsubstituted or substituted by halogen.

$R_8$, $R_9$ and $R_{10}$ are each independently $C_1$-$C_4$alkyl which is unsubstituted or substituted by halogen, or are $C_2$-$C_4$alkenyl, $C_3$-$C_6$alkynyl, phenyl or phenyl which is substituted by halogen, $C_1$-$C_3$alkyl, $C_1$-$C_3$alkoxy, trifluoromethyl or nitro, or are benzyl or benzyl which is substituted by halogen or nitro, $R_{11}$ is hydrogen, $C_1$-$C_8$alkyl or $C_1$-$C_3$alkoxy, or $R_{10}$ and $R_{11}$, together with the nitrogen atom to which they are attached, are a 5- or 6-membered heterocyclic ring system which may contain a further hetero atom selected from the group consisting of N, O and S.

A heterocyclic ring system $R_7$ may be saturated, partly saturated or unsaturated and is for example thiophene, furan, tetrahydrofuran and pyrimidine.

A heterocyclic ring system —$NR_{10}R_{11}$ may be saturated, partly saturated or unsaturated and is for example pyrrolidine, pyrroline, pyrrole, imidazolidine, imidazoline, piperazine, pyridine, pyrimidine, pyrazine, thiazine, oxazole, thiazole and, in particular, piperidine and morpholine.

Depending on the indicated number of carbon atoms, alkyl as moiety of the acylated amidoxime group Z may be any straight chain and any branched alkyl group.

$R_7$ as $C_3$–$C_6$cycloalkyl is cyclopropyl, cyclobutyl, cyclopentyl and cyclohexyl.

The $C_2$–$C_4$alkenyl and $C_3$–$C_6$alkynyl moieties of the acylated amidoxime group Z are preferably vinyl, allyl, 1-propenyl, isopropenyl and propynyl.

Z as an esterified carboxyl group or thiocarbonyl group is a corresponding acid radical which is esterified for example by an unsubstituted or substituted aliphatic radical or by an unsubstituted or substituted cycloaliphatic, aromatic or heterocyclic radical which may be bound through an aliphatic radical.

The preferred esterified carboxyl group is the —$COOR_{12}$ group and the preferred thiocarbonyl group is the —$COSR_{13}$ group, wherein $R_{12}$ and $R_{13}$ have the following meanings: unsubstituted or substituted alkyl, alkenyl, alkynyl, cycloalkyl, phenyl or naphthyl, or an unsubstituted or substituted heterocyclic radical. The —$COOR_{12}$ and —$COSR_{13}$ radicals also include the free acids, where $R_{12}$ and $R_{13}$ are hydrogen, and the salts thereof, where $R_{12}$ and $R_{14}$ are a cation. Suitable salt-forming metals are alkaline earth metals such as magnesium or calcium. Other suitable salt formers are transition metals, for example, iron, nickel, cobalt, copper, zinc, chromium or manganese. Examples of suitable salt forming bases are primary, secondary or tertiary aliphatic and aromatic amines which may be hydroxylated at the hydrocarbon radical, for example methylamine, ethylamine, propylamine, isopropylamine, the 4 isomers of butylamine, dimethylamine, diethylamine, dipropylamine, diisopropylamine, di-n-butylamine, pyrrolidine, piperidine, morpholine, trimethylamine, triethylamine, tripropylamine, quinuclidine, pryidine, quinoline, isoquinoline, as well as methanolamine, ethanolamine, propanolamine, dimethylolamine, diethanolamine or triethanolamine. Suitable organic nitrogen bases are also quaternary ammonium bases. Examples of quaternary ammonium bases are tetraalkylammonium cations in which the alkyl moieties are each independently straight chain or branched $C_1$–$C_6$alkyl groups, for example the tetramethylammonium cation, the tetraethylammonium cation or the trimethylethylammonium cation, and also the trimethylbenzylammonium cation, the triethylbenzylammonium cation and the trimethyl-2-hydroxyethylammonium cation. Particularly preferred salt formers are the ammonium cation and the trialkylammonium cations in which the alkyl moieties are each independently straight chain or branched $C_1$–$C_6$alkyl groups which are unsubstituted or substituted by a hydroxyl group, preferably $C_1$–$C_2$alkyl groups. Such cations are for example the trimethylammonium cation, the triethylammonium cation and the tri-(2-hydroxyethyl)ammonium cation.

Z as a carbamoyl group is a corresponding amide group which may be unsubstituted or mono- or disubstituted at the nitrogen atom, or in which the nitrogen atom forms part of an unsubstituted or substituted heterocyclic radical. Eligible substituents of the amide group are for example an unsubstituted or substituted aliphatic radical which may be bound through an oxygen atom, an unsubstituted or substituted cycloaliphatic, aromatic or heterocyclic radical which may be bound through an aliphatic radical, or an unsubstituted or mono- or disubstituted amino group.

The preferred carbamoyl radical is the —$CONR_{14}R_{15}$ radical, wherein $R_{14}$ is hydrogen, an unsubstituted or substituted alkyl, alkenyl, alkynyl, cycloalkyl, phenyl or naphthyl radical, an unsubstituted or substituted heterocyclic radical or an alkoxy radical, $R_{15}$ is hydrogen, amino, monosubstituted or disubstituted amino or an unsubstituted or substituted alkyl, alkenyl, cycloalkyl or phenyl radical, or —$NR_{14}R_{15}$ is unsubstituted or substituted heterocyclic radical.

Suitable substituents of the organic radicals $R_{12}$, $R_{13}$, $R_{14}$ and $R_{15}$ are for example halogen, nitro, cyano, hydroxy, alkyl, haloalkyl, alkoxy which may be interrupted by one or more oxygen atoms, alkylthio, haloalkoxy, hydroxyalkyl which may be interrupted by one or more oxygen atoms, hydroxyalkylthio, alkoxycarbonyl, amino, alkylamino, dialkylamino, hydroxyalkylamino, di(hydroxyalkyl)amino, aminoalkylamino, cycloalkyl, phenyl or substituted phenyl, phenoxy or substituted phenoxy, or an unsubstituted or substituted heterocyclic radical.

Heterocyclic radicals as moieties of the esterified carboxyl group, of the thiocarbonyl group and of the carbamoyl group will preferably be understood to mean 5- or 6-membered saturated or unsaturated, unsubstituted or substituted monocyclic heterocycles containing 1 to 3 heteroatoms selected from the group consisting of N, O and S, and are for example furan, tetrahydrofuran, tetrahydropyran, tetrahydropyrimidine, pyridine, piperidine, morpholine and imidazole.

Cycloalkyl radicals as moieties of the esterified carboxyl group, of the thiocarbonyl group and of the carbamoyl group will preferably be understood to mean those containing 3 to 8, in particular 3 to 6, carbon atoms.

Aliphatic, acyclic radicals present in the substituent Z as moiety of the esterified carboxyl group, of the thiocarbonyl group and of the carbamoyl group may be straight chain or branched and preferably contain a maximum of 18 carbon atoms. A smaller number of carbon atoms is frequently advantageous, especially in composite substituents.

Z as a cyclised derivative of a carbamoyl group is preferably an unsubstituted or substituted oxazolin-2-yl radical, most preferably an unsubstituted oxazolin-2-yl radical.

A and Z together can form an unsubstituted or substituted tetrahydrofuran-2-one ring. The unsubstituted tetrahydrofuran-2-one ring is preferred, in particular the unsubstituted tetrahydrofuran-2-on-3-yl ring.

In the compounds of formula I, halogen denotes fluorine, chlorine, bromine and iodine, with chlorine, bromine and iodine being preferred.

Suitable salt formers are organic and inorganic acids. Examples of organic acids are acetic acid, trichloroacetic acid, oxalic acid, benzenesulfonic acid and methanesulfonic acid. Examples of inorganic acids are hydrochloric acid, hydrobromic acid, hydriodic acid, sulfuric acid, phosphoric acid, phosphorous acid and nitric acid.

Examples of suitable metal complex formers are elements of the 3rd and 4th main groups of the Periodic Table, for example aluminium, tin and lead; and of the 1st to 8th auxiliary groups, for example chromium, manganese, iron, cobalt, nickel, zirconium, zinc, copper, silver and mercury. The auxiliary group elements of the 4th period are preferred.

Where A is —CH(CH$_3$)— in the compounds of formula I, or A and Z together form a tetrahydrofuran-2-one ring, optical isomers are obtained. Within the scope of the present invention, the compounds of formula I will be understood as comprising both the optically pure isomers and mixtures of isomers.

Compounds particularly suitable for the use in the practice of this invention are those of the formula I, wherein (a) R$_1$ is hydrogen or halogen, where halogen denotes preferably chlorine, iodine and bromine, R$_2$ is hydrogen, R$_3$ is hydrogen, halogen or nitro, where halogen preferably denotes chlorine and bromine, R$_4$ and R$_5$ are hydrogen and R$_6$ is hydrogen or C$_1$–C$_6$alkyl, where alkyl is preferably methyl;

(b) A is —CH$_2$—;

(c) A is —CH$_2$CH$_2$—;

(d) A is —CH(CH$_3$)—;

(e) Z is the amidoxime group

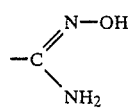

(f) Z is an acylated amidoxime group

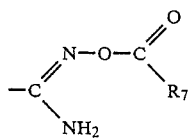

wherein R$_7$ is C$_1$–C$_4$alkyl which is unsubstituted or mono- or disubstituted by halogen, preferably chlorine or bromine, or monosubstituted by alkoxy, or is cyclopropyl, C$_2$–C$_3$alkenyl, phenyl or phenyl which is monosubstituted by halogen, preferably chlorine, or is benzyl, or is furanyl or furanyl which is substituted by halogen, preferably bromine, or is tetrahydrofuranyl, thienyl or dihalogenated pyrimidine, for example dichloropyrimidine;

(g) Z is an acylated amidoxime group

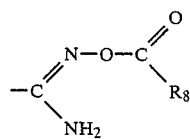

wherein R$_8$ is C$_1$–C$_4$alkyl which is unsubstituted or monosubstituted by halogen, preferably bromine, or is allyl, phenyl or benzyl;

(h) Z is an acylated amidoxime group

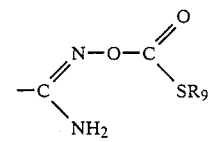

wherein R$_9$ is C$_1$–C$_5$alkyl;

(i) Z is an acylated amidoxime group

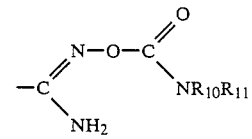

wherein R$_{10}$ is C$_1$–C$_4$alkyl or phenyl or phenyl which is mono- or disubstituted by halogen, preferably chlorine, or is monosubstituted by trihalomethyl, preferably trifluoromethyl, and R$_{11}$ is hydrogen or methoxy;

(k) Z is the esterified carboxyl group —COOR$_{12}$, wherein R$_{12}$ is hydrogen, an alkali metal cation, preferably a sodium or potassium cation, the ammonium cation or an ammonium cation which is trisubstituted by C$_1$–C$_4$alkyl or monohydroxy-C$_1$–C$_4$alkyl, for example hydroxyethyl, or is C$_1$–C$_{12}$alkyl, or is C$_1$–C$_4$alkyl which is monosubstituted by halogen, preferably chlorine, or by C$_1$–C$_3$alkoxy, phenoxy, phenyl or tetrahydrofuranyl, or is C$_2$–C$_4$alkenyl, preferably methyallyl, or is C$_3$–C$_4$alkynyl, preferably 2-propynyl, or is cyclohexyl, phenyl or phenyl which is mono- or disubstituted by methyl;

(l) Z is the alkylthiocarbonyl group —COSR$_{13}$, wherein R$_{13}$ is C$_5$–C$_{10}$alkyl, preferably n-octyl;

(m) Z is the dialkylcarbamoyl group —CONR$_{14}$R$_{15}$, wherein R$_{14}$ is hydrogen, C$_1$–C$_{12}$alkyl, preferably C$_1$–C$_4$alkyl or C$_1$–C$_4$alkyl which is monosubstituted by hydroxy, C$_1$–C$_4$alkoxy, di(C$_1$–C$_4$alkyl)amino, (monohydroxy-C$_1$–C$_4$alkyl)amino, di(monohydroxy-C$_1$–C$_4$alkyl)amino, phenyl, tetrahydrofuranyl, piperidinyl or morpholinyl, or is allyl, cyclohexyl or amino, and R$_{15}$ is hydrogen, C$_1$–C$_4$alkyl or monohydroxy-C$_1$–C$_4$alkyl, or wherein —NR$_{14}$R$_{15}$ form the morpholino ring; or (n) A and Z together are tetrahydrofuran-2-one.

Particularly preferred compounds of formula I are those wherein simultaneously R$_1$, R$_2$, R$_3$, R$_4$, R$_5$ and R$_6$ have one of the meanings as defined in (a), A has one of the meanings as defined in (b) to (d), and Z has one of the meanings as defined in (e) to (m), or A and Z together are as defined in (n); and, in particular, the following group of compounds of formula I, wherein R$_1$ is hydrogen, chlorine, bromine or iodine, R$_2$ is hydrogen, R$_3$ is hydrogen, chlorine, bromine or iodine, R$_4$ and R$_5$ are hydrogen, R$_6$ is hydrogen or methyl, A is a group selected from —CH$_2$—, —CH$_2$CH$_2$— or —CH(CH$_3$)—, and Z is cyano

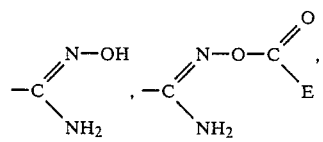

—COOR$_{12}$, —COSR$_{13}$ or —CONR$_{14}$R$_{15}$ wherein E is —R$_7$, —OR$_8$, —SR$_9$ or —NR$_{10}$R$_{11}$ and R$_7$ is C$_1$–C$_4$alkyl which is unsubstituted or mono- or disubstituted by chlorine or bromine, or monosubstituted by $C_1$–$C_4$alkoxy, or is cyclopropyl, $C_2$–$C_3$alkenyl, phenyl or phenyl which is monosubstituted by chlorine, or is benzyl, furanyl or furanyl which is monosubstituted by bromine, or is tetrahydrofuranyl, thienyl or dichloropyrimidine; $R_8$ is $C_1$–$C_4$alkyl which is unsubstituted or monosubstituted by bromine, or is allyl, phenyl or benzyl; $R_9$ is $C_1$–$C_5$alkyl; $R_{10}$ is $C_1$–$C_4$alkyl or phenyl or phenyl which is mono- or disubstituted by chlorine or monosubstituted by trifluoromethyl; $R_{11}$ is hydrogen or methoxy; $R_{12}$ is hydrogen, the sodium cation, the potassium cation, the ammonium cation, an ammonium cation which is trisubstituted by $C_1$–$C_4$alkyl or 2-hydroxyethyl; or is $C_1$–$C_8$alkyl or $C_1$–$C_4$alkyl which is monosubstituted by chlorine, $C_1$–$C_3$alkoxy, phenoxy, phenyl or tetrahydrofuranyl; or is methylallyl, 2-propynyl, cyclohexyl, phenyl or phenyl which is mono- or disubstituted by methyl; $R_{13}$ is n-octyl; $R_{14}$ is hydrogen, $C_1$–$C_4$alkyl, $C1$–$C_4$alkyl which is monosubstituted by hydroxy, $C_1$–$C_4$alkoxy, di($C_1$–$C_4$alkyl)amino, phenyl, tetrahydrofuranyl, piperidinyl or morpholinyl; or is allyl, cyclohexyl or amino; and $R_{15}$ is hydrogen, $C_1$–$C_4$alkyl or monohydroxy-$C_1$–$C_4$alkyl; or —$NR_{14}R_{15}$ forms the morpholino ring; or A and Z together are tetrahydrofuran-2-one.

Particularly interesting compounds of formula I are those wherein $R_1$, $R_2$, $R_4$, $R_5$ and $R_6$ are hydrogen or chlorine, A is the —$CH_2$— group and Z is cyano, an acylated amidoxime group

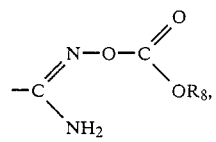

wherein $R_8$ is $C_1$–$C_4$alkyl, preferably methyl, or an esterified carboxyl group —$COOR_{12}$, wherein $R_{12}$ is $C_1$–$C_8$alkyl, preferably n-butyl, 1-methylhexyl, or $C_2$–$C_4$alkenyl, preferably methylallyl.

Examples of compounds suitable for use in the practice of this invention are listed in the following Table 1.

Individual compounds to be singled out for special mention are:
5-chloro-8-(cyanomethoxy)quinoline,
O-(methoxycarbonyl)-2-(8-quinolinoxy)acetamidoxime,
n-butyl 2-(5-chloro-8-quinolinoxy)acetate,
methylallyl 2-(5-chloro-8-quinolinoxy)acetate and
1-methylhexyl 2-(5-chloro-8-quinolinoxy)acetate.

It is particularly preferred to use 5-chloro-8-cyanomethoxy)quinoline, O-methoxycarbonyl-2-(8-quinolinoxy)acetamidoxime, n-butyl 2-(5-chloro-8-quinolinoxy)acetate, 1-methylhexyl 2-(5-chloro-8-quinolinoxy)acetate or methylallyl 2-(5-chloro-8-quinolinoxy)acetate for protecting cultivated plants, especially cereals from the harmful effects of 2-[4,5-dihydro-5-methyl-(1-methylethyl)-4-oxo-1H-imidazol-2-yl]nicotinic acid or 2-[4,5-dihydro-5-methyl-(1-methylethyl)-4-oxo-1H-imidazol-2-yl]-3-quinolinecarboxylic acid.

TABLE 1 (I)

| No. | $R_1$ | $R_2$ | $R_3$ | $R_4$ | $R_5$ | $R_6$ | A | Z | Physical data (°C) |
|---|---|---|---|---|---|---|---|---|---|
| 1 | H | H | H | H | H | H | —$CH_3$— | —CN | m.p. 118–119° |
| 2 | H | H | H | H | H | H | —$CH_2$— | —C(=NOH)NH$_2$ | m.p. 201–204° C. (dec) |
| 3 | H | H | H | H | H | $CH_3$ | —$CH_2$— | —CN | m.p. 114–116° |
| 4 | H | H | H | H | H | $CH_3$ | —$CH_2$— | —C(=NOH)NH$_2$ | m.p. 209–210° (dec) |
| 5 | H | H | Cl | H | H | H | —$CH_2$— | —C(=NOH)NH$_2$ | m.p. 203–205° (dec) |
| 6 | H | H | H | H | H | H | —$CH_2$— | —C(NH$_2$)=N—O—C(=O)NH—C$_3$H$_7$iso | m.p. 136–138° |
| 7 | H | H | Cl | H | H | H | —$CH_2$— | —CN | m.p. 159–160° |

TABLE 1-continued

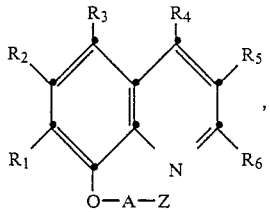
(I)

| # | R1 | R2 | R3 | R4 | R5 | R6 | A | Z | m.p. |
|---|----|----|----|----|----|----|---|---|------|
| 8 | H | H | H | H | H | H | —CH2— | ![structure: -C(NH2)=N-O-C(=O)-CH2Cl] | m.p. 129–130° |
| 9 | Br | H | Cl | H | H | H | —CH2— | ![structure: -C(NH2)=NOH] | m.p. 197–198° (dec) |
| 10 | Br | H | Cl | H | H | H | —CH2— | —CN | m.p. 150–151° |
| 11 | H | H | H | H | H | H | —CH2— | ![structure: -C(NH2)=N-O-C(=O)-OCH3] | m.p. 143–145° |
| 12 | I | H | Cl | H | H | H | —CH2— | ![structure: -C(NH2)=NOH] | m.p. 195–196° (dec) |
| 13 | I | H | Cl | H | H | H | —CH2— | —CN | m.p. 141–143° |
| 14 | Br | H | Cl | H | H | H | —CH2— | ![structure: -C(NH2)=N-O-C(=O)-NH-C3H7iso] | m.p. 162–165° |
| 15 | Cl | H | Cl | H | H | CH3 | —CH2— | ![structure: -C(NH2)=NOH] | m.p. 205–207° (dec) |
| 16 | Cl | H | Cl | H | H | H | —CH2— | —CN | m.p. 150–152° |
| 17 | I | H | Cl | H | H | H | —CH2— | ![structure: -C(NH2)=N-O-C(=O)-NH-C3H7iso] | m.p. 163–167° |
| 18 | Cl | H | Cl | H | H | CH3 | —CH2— | —CN | m.p. 157–158° |
| 19 | Cl | H | Cl | H | H | CH3 | —CH2— | ![structure: -C(NH2)=N-O-C(=O)-NH-C3H7iso] | m.p. 149–152° |
| 20 | H | H | H | H | H | H | —CH2—CH2— | —CN | m.p. 108–112° |
| 21 | H | H | H | H | H | H | —CH(CH3)— | —CN | m.p. 121–124° |

TABLE 1-continued $$\text{(I)}$$

Structure (I): benzene ring with substituents $R_1$ (para to O-A-Z), $R_2$, $R_3$, connected via =CH-C(=N)- side chain bearing $R_4$, $R_5$, $R_6$; ortho position bears O-A-Z group.

| | $R_1$ | $R_2$ | $R_3$ | $R_4$ | $R_5$ | $R_6$ | A | Z | |
|---|---|---|---|---|---|---|---|---|---|
| 22 | H | H | H | H | H | H | $-CH_2-CH_2-$ | $-C(=NOH)NH_2$ | m.p. 186–189° |
| 23 | H | H | Cl | H | H | H | $-CH(CH_3)-$ | $-CN$ | m.p. 143–145° |
| 24 | H | H | H | H | H | H | $-CH(CH_3)-$ | $-C(=NOH)NH_2$ | m.p. 191–194° (dec) |
| 25 | H | H | Cl | H | H | H | $-CH(CH_3)-$ | $-C(=NOH)NH_2$ | m.p. 186–189° (dec) |
| 26 | H | H | $NO_2$ | H | H | H | $-CH(CH_3)-$ | $-CN$ | m.p. 154–156° |
| 27 | Cl | H | $NO_2$ | H | H | H | $-CH_2-$ | $-C(=NOH)NH_2$ | m.p. 214–216° (dec) |
| 28 | Cl | H | $NO_2$ | H | H | H | $-CH_2-$ | $-CN$ | m.p. 166–169° |
| 29 | H | H | H | H | H | H | $-CH_2-$ | $-C(NH_2)=N-O-C(=O)-\text{cyclopropyl}$ | m.p. 165–166° |
| 30 | H | H | H | H | H | H | $-CH_2-$ | $-C(NH_2)=N-O-C(=O)-\text{(4-Cl-phenyl)}$ | m.p. 139–141° |
| 31 | H | H | Cl | H | H | H | $-CH_2-$ | $-C(NH_2)=N-O-C(=O)CH_3$ | m.p. 141–143° |
| 32 | H | H | $NO_2$ | H | H | H | $-CH_2-$ | $-CN$ | m.p. 162–164° |
| 33 | H | H | $NO_2$ | H | H | H | $-CH_2-$ | $-C(=NOH)NH_2$ | m.p. 212–215° (dec) |

TABLE 1-continued

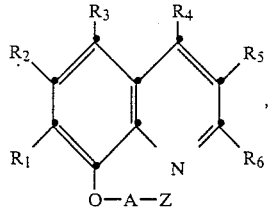

(I)

| No. | $R_1$ | $R_2$ | $R_3$ | $R_4$ | $R_5$ | $R_6$ | A | Z | |
|---|---|---|---|---|---|---|---|---|---|
| 34 | H | H | Cl | H | H | H | —CH$_2$— | $-\underset{\underset{NH_2}{\|}}{C}=N-O-\underset{\underset{OCH_3}{\|}}{\overset{O}{\|}}$ | m.p. 148–149° |
| 35 | H | H | Cl | H | H | H | —CH$_2$— | $-\underset{\underset{NH_2}{\|}}{C}=N-O-\underset{\underset{O-C_2H_5}{\|}}{\overset{O}{\|}}$ | m.p. 139–140° |
| 36 | H | H | H | H | H | H | —CH$_2$— | $-\underset{\underset{NH_2}{\|}}{C}=N-O-\underset{\underset{S-C_5H_{11}n}{\|}}{\overset{O}{\|}}$ | m.p. 111–114° |
| 37 | H | H | H | H | H | H | —CH$_2$— | $-\underset{\underset{NH_2}{\|}}{C}=N-O-\underset{\underset{\underset{CH_3}{\|}}{\underset{CH}{\|}}}{\overset{O}{\|}}$CH | m.p. 158–162° |
| 38 | H | H | H | H | H | H | —CH$_2$— | $-\underset{\underset{NH_2}{\|}}{C}=N-O-\underset{\underset{C_2H_5}{\underset{NH}{\|}}}{\overset{O}{\|}}$ | m.p. 123–125° |
| 39 | H | H | H | H | H | H | —CH$_2$— | $-\underset{\underset{NH_2}{\|}}{C}=N-O-\underset{\underset{\underset{OCH_3}{\|}}{\underset{N-CH_3}{\|}}}{\overset{O}{\|}}$ | m.p. 138–139° |
| 40 | H | H | H | H | H | H | —CH$_2$— | $-\underset{\underset{NH_2}{\|}}{C}=N-O-\underset{\underset{C_4H_9n}{\|}}{\overset{O}{\|}}$ | m.p. 120–122° (dec) |
| 41 | H | H | Cl | H | H | H | —CH$_2$— | $-\underset{\underset{NH_2}{\|}}{C}=N-O-\underset{\underset{C_2H_5}{\|}}{\overset{O}{\|}}$ | m.p. 157–158° (dec) |
| 42 | H | H | H | H | H | H | —CH$_2$— | $-\underset{\underset{NH_2}{\|}}{C}=N-O-\underset{\underset{\underset{CH_2Cl}{\|}}{\underset{CH_2}{\underset{CH_2}{\|}}}}{\overset{O}{\|}}$ | m.p. 144–146° |

TABLE 1-continued

Structure (I):

Phenyl ring with substituents $R_1$, $R_2$, $R_3$ (and CH$_3$), connected via CH to pyridine ring bearing $R_4$, $R_5$, $R_6$ with N and O–A–Z group.

| No. | $R_1$ | $R_2$ | $R_3$ | $R_4$ | $R_5$ | $R_6$ | A | Z | m.p. |
|---|---|---|---|---|---|---|---|---|---|
| 43 | H | H | H | H | H | H | –CH$_2$– | –C(NH$_2$)=N–O–C(O)–CHCl–CH$_2$Cl | m.p. 112–114° |
| 44 | H | H | Cl | H | H | H | –CH$_2$– | –C(NH$_2$)=N–O–C(O)–C$_3$H$_7$iso | m.p. 173–174° |
| 45 | H | H | H | H | H | H | –CH$_2$– | –C(NH$_2$)=N–O–C(O)–O–C$_6$H$_5$ | m.p. 155–156° |
| 46 | H | H | H | H | H | H | –CH$_2$– | –C(NH$_2$)=N–O–C(O)–C$_4$H$_9$t-C$_4$H$_9$ | m.p. 107–110.5° |
| 47 | H | H | H | H | H | H | –CH$_2$– | –C(NH$_2$)=N–O–C(O)–C$_4$H$_9$iso | m.p. 124–126° |
| 48 | H | H | H | H | H | H | –CH$_2$– | –C(NH$_2$)=N–O–C(O)–(2-Cl-C$_6$H$_4$) | m.p. 131–132° |
| 49 | H | H | H | H | H | H | –CH$_2$– | –C(NH$_2$)=N–O–C(O)–CH$_2$–O–sec-C$_4$H$_9$ | m.p. 84–86° |
| 50 | H | H | H | H | H | H | –CH$_2$– | –C(NH$_2$)=N–O–C(O)–(2-furyl) | m.p. 168–169° |

TABLE 1-continued
| | $R_1$ | $R_2$ | $R_3$ | $R_4$ | $R_5$ | $R_6$ | A | Z | |
|---|---|---|---|---|---|---|---|---|---|
| 51 | H | H | H | H | H | H | —CH$_2$— | 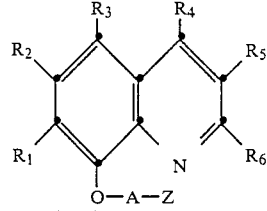 | m.p. 100–103° |
| 52 | H | H | Cl | H | H | H | —CH$_2$— | 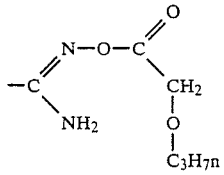 | m.p. 156–157° (dec) |
| 53 | H | H | H | H | H | H | —CH$_2$— | 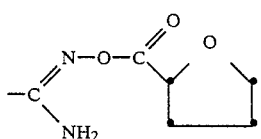 | m.p. 82–85° |
| 54 | H | H | H | H | H | H | —CH$_2$— | 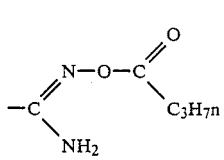 | m.p. 144–147° |
| 55 | H | H | H | H | H | H | —CH$_2$— | 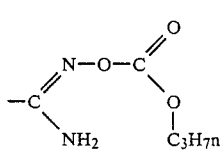 | m.p. 128–130° |
| 56 | H | H | H | H | H | H | —CH$_2$— | 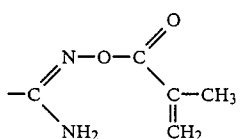 | m.p. 90–92° |
| 57 | H | H | H | H | H | H | —CH$_2$— | 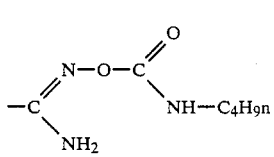 | m.p. 132–134° |
| 58 | H | H | H | H | H | H | —CH$_2$— | 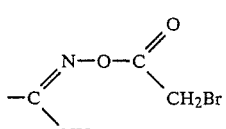 | m.p. 138–140° |
| 59 | H | H | H | H | H | H | —CH$_2$— | 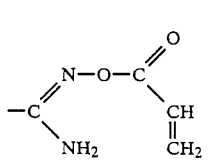 | m.p. 129–131° |

TABLE 1-continued

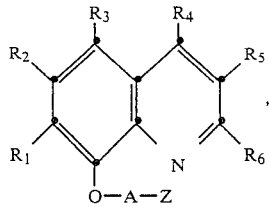

(I)

| No. | R1 | R2 | R3 | R4 | R5 | R6 | A | Z | m.p. |
|---|---|---|---|---|---|---|---|---|---|
| 60 | H | H | H | H | H | H | —CH₂— | =N—O—C(=O)—O—C₄H₉n, with —C(NH₂)= | m.p. 121–123° |
| 61 | H | H | H | H | H | H | —CH₂— | =N—O—C(=O)—O—CH₂—CH=CH₂, with —C(NH₂)= | m.p. 123–125° |
| 62 | H | H | H | H | H | H | —CH₂— | =N—O—C(=O)—O—CH₂—CH₂Br, with —C(NH₂)= | m.p. 127–128° (dec) |
| 63 | H | H | Cl | H | H | H | —CH₂— | =N—O—C(=O)-cyclopropyl, with —C(NH₂)= | m.p. 173–175° |
| 64 | H | H | H | H | H | H | —CH₂— | =N—O—C(=O)—O—CH₂—C₆H₅, with —C(NH₂)= | m.p. 135–137° |
| 65 | H | H | Cl | H | H | H | —CH₂— | =N—O—C(=O)-furyl, with —C(NH₂)= | m.p. 191–192° (dec) |
| 66 | H | H | H | H | H | H | —CH₂— | =N—O—C(=O)—S—C₂H₅, with —C(NH₂)= | m.p. 120–121° |
| 67 | H | H | H | H | H | H | —CH₂— | =N—O—C(=O)—O—CH₂—O—CH₃, with —C(NH₂)= | m.p. 118–120° |

TABLE 1-continued
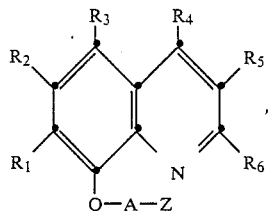
(I)
| | R1 | R2 | R3 | R4 | R5 | R6 | A | Z | |
|---|---|---|---|---|---|---|---|---|---|
| 68 | H | H | Cl | H | H | H | —CH2— | 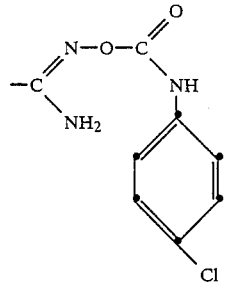 | m.p. 191–192° (dec) |
| 69 | H | H | H | H | H | H | —CH2— | 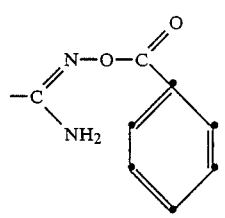 | m.p. 158–159° |
| 70 | H | H | H | H | H | H | —CH2— | 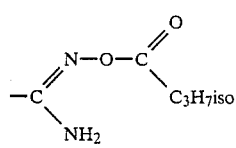 | m.p. 115–117.5° |
| 71 | H | H | H | H | H | H | —CH2— | 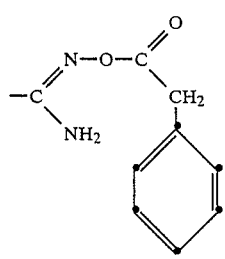 | m.p. 140–142° |
| 72 | H | H | H | H | H | H | —CH2— | 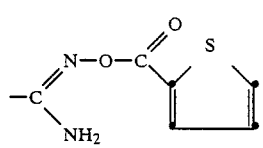 | m.p. 164–165° |
| 73 | H | H | H | H | H | H | —CH2— | 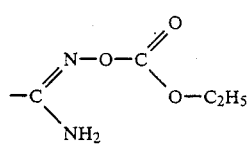 | m.p. 129–132° |

TABLE 1-continued
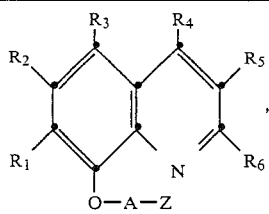
(I)
| | R1 | R2 | R3 | R4 | R5 | R6 | A | Z | |
|---|---|---|---|---|---|---|---|---|---|
| 74 | H | H | H | H | H | H | —CH$_2$— | 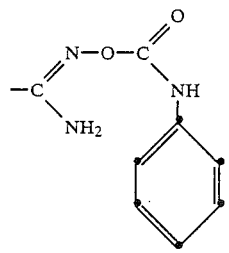 | m.p. 155–157.5° |
| 75 | H | H | H | H | H | H | —CH$_2$— | 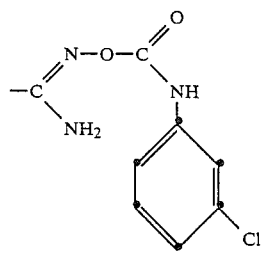 | m.p. 158–160° |
| 76 | H | H | Cl | H | H | H | —CH$_2$— | 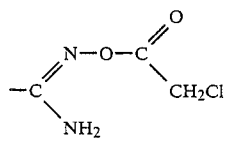 | m.p. 155–158° (dec) |
| 77 | H | H | H | H | H | H | —CH$_2$— | 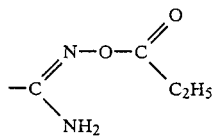 | m.p. 144–146° |
| 78 | H | H | H | H | H | H | —CH$_2$— | 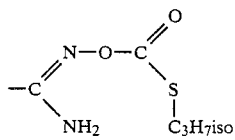 | m.p. 123–124° |
| 79 | H | H | H | H | H | H | —CH$_2$— | 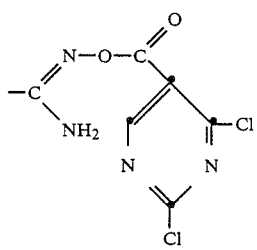 | m.p. 173–176° (dec) |
| 80 | H | H | H | H | H | H | —CH$_2$— | 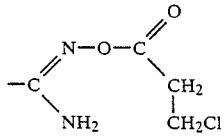 | m.p. 134–136° (dec) |

TABLE 1-continued $$\text{(I)}$$

Structure: Formula (I) - benzopyran-type with substituents R1, R2, R3 on one ring, R4, R5, R6 on the other, and O-A-Z group.

| No. | R1 | R2 | R3 | R4 | R5 | R6 | A | Z | properties |
|---|---|---|---|---|---|---|---|---|---|
| 81 | H | H | H | H | H | H | —CH₂— | —C(NH₂)=N—O—C(=O)—CH₃ | m.p. 100–102° |
| 82 | H | H | H | H | H | H | —CH₂— | —C(NH₂)=N—O—C(=O)—NH—(2,5-dichlorophenyl) | m.p. 197–199° |
| 83 | H | H | H | H | H | H | —CH₂— | —C(NH₂)=N—O—C(=O)—(5-bromo-2-furyl) | m.p. 170–171° |
| 84 | Cl | H | Cl | H | H | H | —CH(CH₃)— | —COOCH₃ | m.p. 65–66° |
| 85 | H | H | H | H | H | H | —CH(CH₃)— | —COOCH₃ | m.p. 70–72° |
| 86 | H | H | H | H | H | H | —CH₂— | —COOH·H₂O | m.p. 184–185° |
| 87 | H | H | H | H | H | H | —CH₂— | —COOCH₂CH₂OCH₃ | m.p. 80–82° |
| 88 | H | H | H | H | H | H | —CH₂— | —COOCH₃ | m.p. 46.5–67.0° |
| 89 | H | H | H | H | H | H | —CH₂— | —COOC₂H₅·H₂O | m.p. 56–59° |
| 90 | H | H | H | H | H | H | —CH(CH₃)— | —CONH(CH₂)₃OC₂H₅ | m.p. 54–56° |
| 91 | H | H | H | H | H | H | —CH(CH₃)— | —CONHC₂H₅ | m.p. 86–88° |
| 92 | H | H | H | H | H | H | —CH₂— | —COOC₃H₇n | m.p. 28–31° |
| 93 | H | H | H | H | H | H | —CH₂— | —COOC₃H₇iso | $n_D^{23} = 1.5696$ |
| 94 | H | H | H | H | H | H | —CH₂— | —CONHCH₃·H₂O | m.p. 74–81° |
| 95 | H | H | H | H | H | H | —CH₂— | —CON(CH₃)₂ | m.p. 142–145° |
| 96 | H | H | H | H | H | H | —CH₂— | —CONHC₂H₅ | $n_D^{22.5} = 1.6002$ |
| 97 | H | H | H | H | H | H | —CH(CH₃)— | —CONH(CH₂)₃OH | m.p. 120–122° |
| 98 | H | H | H | H | H | H | —CH₂— | —COOCH₂CH₂OC₂H₅ | $n_D^{24} = 1.5673$ |

TABLE 1-continued

Structure (I):

R₁, R₂, R₃ on left benzene ring; R₄, R₅, R₆ on right pyridine-type ring; O—A—Z substituent.

| No. | R₁ | R₂ | R₃ | R₄ | R₅ | R₆ | A | Z | Physical data |
|---|---|---|---|---|---|---|---|---|---|
| 99 | H | H | H | H | H | H | —CH(CH₃)— | —CONHCH₂—C₆H₅ | m.p. 88–90° |
| 100 | H | H | H | H | H | H | —CH₂— | —CONH(CH₂)₃CH₃ | m.p. 66–68° |
| 101 | H | H | H | H | H | H | —CH(CH₃)— | —CON(CH₃)(CH₂CH₂OH) | $n_D^{22} = 1.6054$ |
| 102 | H | H | H | H | H | H | —CH₂— | —CON(CH₃)(CH₂CH₂OH) | m.p. 146–149° |
| 103 | H | H | H | H | H | H | —CH₂— | —COOCH₂-(tetrahydrofuran-2-yl) | viscous substance |
| 104 | H | H | H | H | H | H | —CH(CH₃)— | —CONH(CH₂)₃CH₃·H₂O | m.p. 73–76° |
| 105 | H | H | H | H | H | H | —CH(CH₃)— | —CON(morpholino) | m.p. 120–121° |
| 106 | H | H | H | H | H | H | —CH(CH₃)— | —CON(CH₃)₂ | m.p. 105–111° |
| 107 | H | H | Cl | H | H | H | —CH₂— | —COOH | m.p. 232–233° |
| 108 | H | H | Cl | H | H | H | —CH₂— | —COOCH₂CH₂OCH₃ | m.p. 97–98° |
| 109 | H | H | Cl | H | H | H | —CH₂— | —COOCH₃ | m.p. 104–105.5° |
| 110 | H | H | Cl | H | H | H | —CH₂— | —COOC₂H₅ | m.p. 116–117° |
| 111 | H | H | Cl | H | H | H | —CH₂— | —COOC₃H₇n | m.p. 108–109° |
| 112 | H | H | Cl | H | H | H | —CH₂— | —CON(CH₃)₂ | m.p. 135–136° |
| 113 | H | H | H | H | H | CH₃ | —CH₂— | —COOCH₃ | m.p. 58–66° |
| 114 | H | H | H | H | H | H | —CH₂— | —COOC₂H₅ | $n_D^{22.5} = 1.5762$ |
| 115 | H | H | Cl | H | H | H | —CH₂— | —COO—t-C₄H₉ | m.p. 63–69° |
| 116 | H | H | H | H | H | H | —CH₂— | —COO—t-C₄H₉ | m.p. 68–70° |
| 117 | H | H | Cl | H | H | H | —CH₂— | —COOCH₂—C≡CH | m.p. 115–116° |
| 118 | H | H | Cl | H | H | H | —CH₂— | —COO—isoC₃H₇ | m.p. 147–148° |
| 119 | H | H | Cl | H | H | H | —CH₂— | —COOCH₂CH₂OC₂H₅ | m.p. 102–104° |
| 120 | H | H | Cl | H | H | H | —CH₂— | —COOCH₂—C₆H₅ | m.p. 110–112° |
| 121 | H | H | Cl | H | H | H | —CH₂— | —COOCH₂—CH=CH₂ | m.p. 98–99° |
| 122 | H | H | Cl | H | H | H | —CH₂— | —COO(CH₂)₁₁CH₃ | m.p. 76–77° |
| 123 | H | H | Cl | H | H | H | —CH₂— | —COO—sec-C₄H₉ | m.p. 110–111° |

TABLE 1-continued

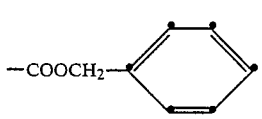

(I)

| # | R1 | R2 | R3 | R4 | R5 | R6 | A | Z | |
|---|----|----|----|----|----|----|----|----|----|
| 124 | H | H | H | H | H | H | —CH$_2$— | —COO(CH$_2$)$_7$CH$_3$ | $n_D^{24}$ = 1.5419 |
| 125 | H | H | Cl | H | H | H | —CH$_2$— | —COOC$_4$H$_9$n | m.p. 90.5–92° |
| 126 | H | H | H | H | H | H | —CH$_2$— | —COO(CH$_2$)$_{11}$CH$_3$ | $n_D^{23}$ = 1.5232 |
| 127 | H | H | H | H | H | H | —CH$_2$— | —COOCH$_2$—CH=CH$_2$ | $n_D^{23}$ = 1.5885 |
| 128 | H | H | Cl | H | H | H | —CH$_2$— | —COO(CH$_2$)$_7$CH$_3$ | m.p. 87–88° |
| 129 | H | H | H | H | H | H | —CH$_2$— | —COOC$_4$H$_9$n | $n_D^{22}$ = 1.5642 |
| 130 | H | H | H | H | H | H | —CH$_2$— | —COO—sec-C$_4$H$_9$ | oil (red) |
| 131 | H | H | Cl | H | H | H | —CH$_2$— | —COOCH$_2$CH$_2$Cl | m.p. 125–126° |
| 132 | H | H | H | H | H | H | —CH$_2$— | 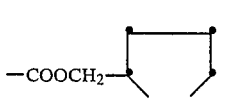 | $n_D^{23.5}$ = 1.6099 |
| 133 | H | H | Cl | H | H | H | —CH$_2$— | 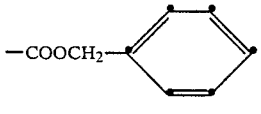 | m.p. 101–103° |
| 134 | H | H | Cl | H | H | H | —CH$_2$— | —COS(CH$_2$)$_7$CH$_3$ | m.p. 53–54° |
| 135 | H | H | H | H | H | H | —CH$_2$— | —COOCH$_2$CH$_2$Cl | m.p. 109–110° |
| 136 | I | H | Cl | H | H | H | —CH$_2$— | —COO—t-C$_4$H$_9$ | m.p. 81–97° |
| 137 | I | H | Cl | H | H | H | —CH$_2$— | —COOC$_2$H$_5$ | m.p. 92–94° |
| 138 | I | H | Cl | H | H | H | —CH$_2$— | —COO(CH$_2$)$_{11}$CH$_3$ | m.p. 51–53° |
| 139 | I | H | Cl | H | H | H | —CH$_2$— | —COOCH$_3$ | m.p. 121–126° |
| 140 | I | H | Cl | H | H | H | —CH$_2$— | —COOCH$_2$CH$_2$Cl | m.p. 44–45° |
| 141 | I | H | Cl | H | H | H | —CH$_2$— | 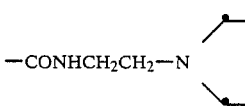 | m.p. 112–113° |
| 142 | I | H | Cl | H | H | H | —CH$_2$— | —COOC$_3$H$_7$n | m.p. 71–73° |
| 143 | H | H | H | H | H | H | —CH$_2$— | —COO—isoC$_4$H$_9$ | $n_D^{22}$ = 1.5632 |
| 144 | H | H | H | H | H | H | —CH$_3$— | —COOCHCH$_2$CH$_2$CH$_3$<br>　　　　\|<br>　　　　CH$_3$ | $n_D^{22}$ = 1.5391 |
| 145 | H | H | H | H | H | H | —CH$_2$— | —COOCH(CH$_2$)$_5$CH$_3$<br>　　　　\|<br>　　　　CH$_3$ | $n_D^{22}$ = 1.5342 |
| 146 | H | H | H | H | H | H | —CH$_2$— | —CONH(CH$_2$)$_{11}$CH$_3$ | m.p. 56–61° |
| 147 | H | H | H | H | H | H | —CH$_2$— | —CONHCH$_2$CH$_2$—N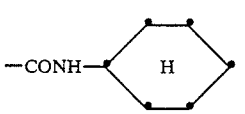O | m.p. 94–99° |
| 148 | H | H | H | H | H | H | —CH$_2$— | —CONHCH$_2$CH$_2$CH$_2$OH | m.p. 138–139° |
| 149 | H | H | H | H | H | H | —CH$_2$— | —CONH—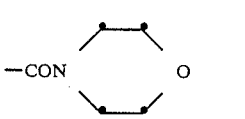—H | m.p. 104–106° |
| 150 | H | H | H | H | H | H | —CH$_2$— | —CONO | m.p. 99–103° |

TABLE 1-continued

Structure (I):

Phenyl ring with substituents $R_1$, $R_2$, $R_3$ and connected via $O-A-Z$; second ring with $R_4$, $R_5$, $R_6$ and N.

| No. | $R_1$ | $R_2$ | $R_3$ | $R_4$ | $R_5$ | $R_6$ | A | Z | Physical data |
|---|---|---|---|---|---|---|---|---|---|
| 151 | H | H | H | H | H | H | $-CH_2-$ | $-CONHCH_2CH_2N(C_2H_5)_2$ | $n_D^{23} = 1.5686$ |
| 152 | H | H | H | H | H | H | $-CH_2-$ | $-CON(CH_2CH_2OH)_2$ | m.p. 144–146° |
| 153 | H | H | H | H | H | H | $-CH_2-$ | $-CONH(CH_2)_3N(CH_3)_2$ | $n_D^{23} = 1.5766$ |
| 154 | H | H | H | H | H | H | $-CH_2-$ | $-CON(CH_3)(C_4H_9n)$ | $n_D^{22} = 1.5840$ |
| 155 | H | H | H | H | H | H | $-CH_2-$ | $-CONHCH_2-C_6H_5 \cdot H_2O$ | m.p. 70.5–73.5° |
| 156 | H | H | H | H | H | H | $-CH_2-$ | $-CONHCH(CH_2CH_3)(CH_2OH)$ | m.p. 150–151° |
| 157 | H | H | H | H | H | H | $-CH_2-$ | $-CON(C_4H_9n)_2 \cdot 2H_2O$ | m.p. 105–106° |
| 158 | H | H | H | H | H | H | $-CH_2-$ | $-CONHCH_2CH_2-N$(morpholinyl) | $n_D^{26} = 1.5821$ |
| 159 | H | H | H | H | H | H | $-CH_2-$ | $-CONH(CH_2)_3N(CH_2CH_2OH)_2$ | m.p. 109–110° |
| 160 | H | H | H | H | H | H | $-CH_2-$ | $-CONHCH_2-CH=CH_2 \cdot H_2O$ | m.p. 71–75° |
| 161 | H | H | H | H | H | H | $-CH_2-$ | $-CONHCH_2-$(tetrahydrofuryl)$\cdot H_2O$ | m.p. 57–58° |
| 162 | H | H | H | H | H | H | $-CH_2-$ | $-CONH(CH_2)_3OC_2H_5$ | m.p. 51–61° |
| 163 | H | H | H | H | H | H | $-CH_2-$ | $-CONHCH_2CH_2NHCH_2CH_2OH$ | m.p. 70–91° |
| 164 | H | H | Cl | H | H | H | $-CH_2-$ | $CONH(CH_2)_3OC_2H_5$ | m.p. 85–88° |
| 165 | H | H | Cl | H | H | H | $-CH_2-$ | $-CON(CH_3)(CH_2CH_2OH)$ | m.p. 187–189° |

TABLE 1-continued

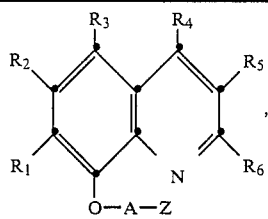

(I)

| | $R_1$ | $R_2$ | $R_3$ | $R_4$ | $R_5$ | $R_6$ | A | Z | |
|---|---|---|---|---|---|---|---|---|---|
| 166 | H | H | Cl | H | H | H | —CH$_2$— | —CON(CH$_2$CH$_2$OH)$_2$ | m.p. 177–179° |
| 167 | H | H | Cl | H | H | H | —CH$_2$— | —CON(morpholino) | m.p. 148–150° |
| 168 | H | H | Cl | H | H | H | —CH$_2$— | —CONHCH$_2$CH$_2$CH$_2$OH | m.p. 157–160° |
| 169 | H | H | Cl | H | H | H | —CH$_2$— | —CONHC$_4$H$_9$n.H$_2$O | m.p. 87–90° |
| 170 | H | H | Cl | H | H | H | —CH$_2$— | —CONHC$_2$H$_5$ | m.p. 94–98° |
| 171 | H | H | Cl | H | H | H | —CH$_2$— | —CONHCH$_2$—C$_6$H$_5$.½H$_2$O | m.p. 146–149° |
| 172 | H | H | H | H | H | CH$_3$ | —CH$_2$— | —CONH$_2$ | m.p. 193–196° |
| 173 | H | H | H | H | H | H | —CH$_2$— | —CONHNH$_2$.H$_2$O | m.p. 121–124° |
| 174 | H | H | H | H | H | H | —CH$_2$— | —COONa.H$_2$O | m.p. 140–142° |
| 175 | H | H | H | H | H | H | —CH$_2$— | —COOK.H$_2$O | m.p. >200° |
| 176 | H | H | H | H | H | H | —CH$_2$— | —COO$^\ominus$ HN(CH$_3$)$_3^\oplus$ | m.p. 176–178° |
| 177 | H | H | H | H | H | H | —CH$_2$— | —COO$^\ominus$ HN(CH$_2$CH$_2$OH)$_3^\oplus$ | m.p. 97–98° |
| 178 | H | H | Cl | H | H | H | —CH$_2$— | —COOK.H$_2$O | m.p. >260° |
| 179 | H | H | Cl | H | H | H | —CH$_2$— | —COONa.H$_2$O | m.p. >260° |
| 180 | H | H | H | H | H | H | —CH$_2$— | —COO$^\ominus$ HN(C$_2$H$_5$)$_3^\oplus$ | m.p. 255–257° (dec) |
| 181 | H | H | Cl | H | H | H | —CH$_2$— | —COO$^\ominus$ NH$_4^\oplus$ | m.p. 227–228° (dec) |
| 182 | H | H | Cl | H | H | H | —CH$_2$— | —COO$^\ominus$ HN(CH$_2$CH$_2$OH)$_3^\oplus$ | m.p. 132–156° (dec) |
| 183 | H | H | Cl | H | H | H | —CH(CH$_3$)— | —COO-(2,4-dimethylphenyl) | m.p. 120–122° |
| 184 | H | H | Cl | H | H | H | —CH$_2$— | —COOCH(CH$_3$)(CH$_2$)$_5$CH$_3$ | m.p. 65–67° |
| 185 | H | H | Cl | H | H | H | —CH$_2$— | —COOCH$_2$CH=CH—CH$_3$ | m.p. 100–102° |
| 186 | H | H | Cl | H | H | H | —CH$_2$— | —COOCH$_2$—C(CH$_3$)=CH$_2$ | m.p. 94–95° |
| 187 | H | H | Cl | H | H | H | —CH$_2$— | —COOCH$_2$CH$_2$OC$_3$H$_7$iso | m.p. 70–72° |

TABLE 1-continued

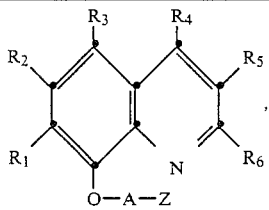

| | R₁ | R₂ | R₃ | R₄ | R₅ | R₆ | A | Z | |
|---|---|---|---|---|---|---|---|---|---|
| 188 | H | H | Cl | H | H | H | —CH₂— | —COOCH₂CH₂—O—C₆H₅ | m.p. 79–80.5° |
| 189 | Br | H | Br | H | H | H | —CH₂— | —COOCH₃ | m.p. 143–145° |
| 190 | Br | H | Cl | H | H | H | —CH₃— | —COOC₃H₇iso | m.p. 71–73° |
| 191 | Br | H | Br | H | H | H | —CH₂— | —COOC₃H₇iso | m.p. 47–51° |
| 192 | Cl | H | Cl | H | H | H | —CH₂— | —COOC₄H₉n | m.p. 42–43.5° |
| 193 | Br | H | Cl | H | H | H | —CH₂— | —COOC₄H$_n$ | m.p. ca. 28° |
| 194 | Cl | H | Cl | H | H | H | —CH₂— | —COO(CH₂)₇CH₃ | m.p. ca. 30° |
| 195 | Br | H | Cl | H | H | H | —CH₂— | —COO(CH₂)₇CH₃ | m.p. 41–42° |
| 196 | Br | H | Cl | H | H | H | —CH₂— | —COOCH(CH₃)(CH₂)₅CH₃ | m.p. 46–48° |
| 197 | Cl | H | Cl | H | H | H | —CH₂— | —COO(CH₂)₁₁CH₃ | m.p. 49–50° |
| 198 | Br | H | Cl | H | H | H | —CH₂— | —COO(CH₂)₁₁CH₃ | m.p. 50–52° |
| 199 | Cl | H | Cl | H | H | H | —CH₂— | —COOCH₂—C₆H₅ | m.p. 79–80° |
| 200 | Br | H | Cl | H | H | H | —CH₂— | —COOCH₂—C₆H₅ | m.p. 100–102° |
| 201 | Br | H | Br | H | H | H | —CH₂— | —COOCH₂—C₆H₅ | m.p. 101–104° |
| 202 | Br | H | Cl | H | H | H | —CH₂— | —COOCH₂CH₂OCH₃ | m.p. 68–70° |
| 203 | Cl | H | Cl | H | H | H | —CH₂— | —COOCH₂CH₂OC₂H₅ | m.p. 81–82° |
| 204 | Br | H | Cl | H | H | H | —CH₂— | —COOCH₂CH₂OC₂H₅ | m.p. 71–72° |
| 205 | Br | H | Cl | H | H | H | —CH₂— | —COOCH₂CH₂OC₃H₇iso | $n_D^{25} = 1.5763$ |
| 206 | Br | H | Cl | H | H | H | —CH₂— | —COOCH₂CH₂O—C₆H₅ | m.p. 80–82° |
| 207 | Cl | H | Cl | H | H | H | —CH₂— | —COOCH₂—(tetrahydrofuryl) | m.p. 77–78° |
| 208 | Br | H | Cl | H | H | H | —CH₂— | —COOCH₂—(tetrahydrofuryl) | m.p. 79–80° |
| 209 | Cl | H | Cl | H | H | H | —CH₂— | —COOCH₂CH=CH₂ | m.p. 72–73° |
| 210 | Br | H | Cl | H | H | H | —CH₂— | —COOCH₂CH=CH₂ | m.p. 66–68.5° |
| 211 | Br | H | Br | H | H | H | —CH₂— | —COOCH₂CH=CH₂ | m.p. 78–79° |
| 212 | Br | H | Cl | H | H | H | —CH₂— | —COOCH₂CH=CH—CH₃ | m.p. 60–64° |
| 213 | Cl | H | Cl | H | H | H | —CH₂— | —COOCH₂—C(CH₃)=CH₂ | m.p. 62–65° |

TABLE 1-continued $$\text{(I)}$$

Structure (I): benzene ring with substituents $R_1$, $R_2$, $R_3$, and $O-A-Z$; attached to $-C(R_4)=C(R_5)-N=R_6$ side chain.

| No. | $R_1$ | $R_2$ | $R_3$ | $R_4$ | $R_5$ | $R_6$ | A | Z | properties |
|---|---|---|---|---|---|---|---|---|---|
| 214 | Br | H | Cl | H | H | H | $-CH_2-$ | $-COOCH_2-C(CH_3)=CH_2$ | m.p. 62–64° |
| 215 | Br | H | Cl | H | H | H | $-CH_2-$ | $-COO-C_6H_{11}$ (cyclohexyl) | m.p. 52–54° |
| 216 | H | H | Cl | H | H | H | $-CH(CH_3)-$ | $-COOC_3H_7\text{iso}$ | $n_D^{24} = 1.5642$ |
| 217 | H | H | Cl | H | H | H | $-CH(CH_3)-$ | $-COO(CH_2)_7CH_3$ | $n_D^{23} = 1.5356$ |
| 218 | H | H | Cl | H | H | H | $-CH(CH_3)-$ | $-COOCH(CH_3)(CH_2)_5CH_3$ | $n_D^{25} = 1.5370$ |
| 219 | H | H | Cl | H | H | H | $-CH(CH_3)-$ | $-COO(CH_2)_{11}CH_3$ | m.p. 54–55° |
| 220 | H | H | Cl | H | H | H | $-CH(CH_3)-$ | $-COOCH_2-C_6H_5$ | m.p. 57–59° |
| 221 | H | H | Cl | H | H | H | $-CH(CH_3)-$ | $-COOCH_2CH_2OC_3H_7\text{iso}$ | $n_D^{32} = 1.5403$ |
| 222 | H | H | Cl | H | H | H | $-CH(CH_3)-$ | $-COOCH_2CH_2O-C_6H_5$ | $n_D^{29} = 1.5962$ |
| 223 | H | H | Cl | H | H | H | $-CH(CH_3)-$ | $-COOCH_2CH=CH_2$ | m.p. 40–41° |
| 224 | H | H | Cl | H | H | H | $-CH(CH_3)-$ | $-COOCH_2CH=CH-CH_3$ | m.p. 39–40° |
| 225 | H | H | Cl | H | H | H | $-CH(CH_3)-$ | $-COOCH_2-C(CH_3)=CH_2$ | m.p. 62–63° |
| 226 | H | H | Cl | H | H | H | $-CH(CH_3)-$ | $-COO-C_6H_{11}$ (cyclohexyl) | $n_D^{30} = 1.5677$ |
| 227 | Br | H | Cl | H | H | H | $-CH(CH_3)-$ | $-COO(CH_2)_7CH_3$ | $n_D^{28} = 1.5439$ |
| 228 | Cl | H | Cl | H | H | H | $-CH(CH_3)-$ | $-COOCH(CH_3)(CH_2)_5CH_3$ | $n_D^{25} = 1.5408$ |

TABLE 1-continued

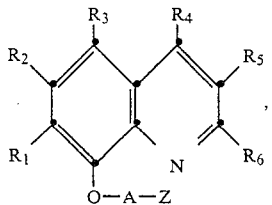

(I)

| No. | R1 | R2 | R3 | R4 | R5 | R6 | A | Z | |
|---|---|---|---|---|---|---|---|---|---|
| 229 | Br | H | Cl | H | H | H | —CH(CH₃)— | —COOCH(CH₃)(CH₂)₅CH₃ | $n_D^{25} = 1.5527$ |
| 230 | Br | H | Cl | H | H | H | —CH(CH₃)— | —COO(CH₂)₁₁CH₃ | $n_D^{30} = 1.5347$ |
| 231 | Br | H | Cl | H | H | H | —CH(CH₃)— | —COOCH₂—C₆H₅ | m.p. 55–56° |
| 232 | Br | H | Cl | H | H | H | —CH(CH₃)— | —COOCH₂—(furyl) | $n_D^{30} = 1.5886$ |
| 233 | Br | H | Cl | H | H | H | —CH(CH₃)— | —COOCH₂CH₂OC₃H₇iso | $n_D^{28} = 1.5642$ |
| 234 | Br | H | Cl | H | H | H | —CH(CH₃)— | —COOCH₂CH₂O—C₆H₅ | $n_D^{20} = 1.6031$ |
| 235 | Br | H | Cl | H | H | H | —CH(CH₃)— | —COOCH₂CH=CH₂ | m.p. 55–56° |
| 236 | Cl | H | Cl | H | H | H | —CH(CH₃)— | —COOCH₂CH=CH—CH₃ | m.p. 38–39° |
| 237 | Br | H | Cl | H | H | H | —CH(CH₃)— | —COOCH₂CH=CH—CH₃ | m.p. 38–40° |
| 238 | Br | H | Cl | H | H | H | —CH(CH₃)— | —COOCH₂C(CH₃)=CH₂ | $n_D^{28} = 1.5824$ |
| 239 | H | H | Cl | H | H | H | —CH₂— | —COO—C₆H₅ | m.p. 165–170° |
| 240 | H | H | Cl | H | H | H | —CH₂— | —COO—C₆H₄—CH₃ | m.p. 143–145° |
| 241 | H | H | Cl | H | H | H | —CH₂— | —COO—C₆H₄(CH₃) (ortho) | m.p. 111–116° |

TABLE 1-continued

Structure (I):

$$\text{R}_2\text{-R}_3\text{-R}_4\text{-R}_5\text{ phenyl with O-A-Z and =N-R}_6$$

| Nr. | R$_1$ | R$_2$ | R$_3$ | R$_4$ | R$_5$ | R$_6$ | A | Z | Physical data (°C.) |
|---|---|---|---|---|---|---|---|---|---|
| 242 | H | H | Cl | H | H | H | —CH$_2$— | —COO—(2,4-dimethylphenyl) | m.p. 108–109° |
| 243 | H | H | Cl | H | H | H | —CH(CH$_3$)— | —COO—phenyl | m.p. 102–105° |

| Nr. | R$_1$ | R$_2$ | R$_3$ | R$_4$ | R$_5$ | R$_6$ | A + Z | Physical data (°C.) |
|---|---|---|---|---|---|---|---|---|
| 244 | H | H | Cl | H | H | H | —CH(CH$_3$)—CH$_2$—O—C(=O)— (lactone ring) | m.p. 140–141.5° |

| No. | R$_1$ | R$_2$ | R$_3$ | R$_4$ | R$_5$ | R$_6$ | A | Z | Physical data (°C.) |
|---|---|---|---|---|---|---|---|---|---|
| 245 | H | H | Cl | H | H | H | —CH$_2$— | —COOCH(CH$_3$)CH$_2$CH$_3$ | m.p. 65–70° |
| 246 | H | H | H | H | H | H | —CH$_2$— | —COOCH$_2$—CH(CH$_3$)(CH$_2$)$_2$CH$_3$ | oil; n$_D^{22}$: 1.5525 |
| 247 | H | H | Cl | H | H | H | —CH$_2$— | —CO—phenyl | m.p. 112–113° |
| 248 | H | H | Cl | H | H | H | —CH$_2$— | —COOCH$_2$CH(CH$_3$)—CH$_3$ | m.p. 113–114° |
| 249 | H | H | H | H | H | H | —CH$_2$— | —COO(CH$_2$)$_2$CH(OCH$_3$)CH$_3$ | oil; n$_D^{23}$: 1.5732 |
| 250 | H | H | H | H | H | H | —CH$_2$— | —COOCH$_2$CH$_2$OCH$_2$CH$_2$O(CH$_2$)$_3$CH$_3$ | oil; n$_D^{22}$: 1.5389 |
| 251 | H | H | H | H | H | H | —CH$_2$— | —COS(CH$_2$)$_3$CH$_3$ | oil; n$_D^{23}$: 1.6096 |
| 252 | H | H | H | H | H | H | —CH$_2$— | —COO—phenyl | oil; n$_D^{23}$: 1.5755 |
| 253 | H | H | H | H | H | H | —CH$_2$— | —COO(CH$_2$)$_4$CH$_3$ | oil; n$_D^{23}$: 1.5591 |
| 254 | H | H | H | H | H | H | —CH$_2$— | —COS(CH$_2$)$_7$CH$_3$ | oil; n$_D^{22}$: 1.5697 |
| 255 | H | H | Cl | H | H | H | —CH$_2$— | —COOCH$_2$—CH(CH$_3$)(CH$_2$)$_2$CH$_3$ | m.p. 74–75° |
| 256 | H | H | Cl | H | H | H | —CH$_2$— | —COS(CH$_2$)$_3$(CH$_3$) | oil; n$_D^{22}$: 1.6076 |
| 257 | H | H | H | H | H | H | —CH$_2$— | —COOCH$_2$CH=CH—CH$_3$ | oil; n$_D^{22}$: 1.5833 |
| 258 | H | H | H | H | H | H | —CH$_2$— | —COOCH$_2$—CH(C$_2$H$_5$)—C$_2$H$_5$ | oil; n$_D^{23}$: 1.5530 |

TABLE 1-continued

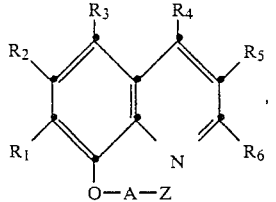

(I)

| # | R1 | R2 | R3 | R4 | R5 | R6 | A | Z | properties |
|---|---|---|---|---|---|---|---|---|---|
| 259 | H | H | Cl | H | H | H | —CH2— | —COOCH2CH2OCH2CH2O(CH2)3CH3 | m.p. 39–41° |
| 260 | H | H | Cl | H | H | H | —CH2— | —COO(CH2)2CHCH3 with OCH3 on CH | m.p. 72–73° |
| 261 | H | H | Cl | H | H | H | —CH2— | —COO(CH2)4CH3 | m.p. 78–79° |
| 262 | H | H | Cl | H | H | H | —CH2— | —COOCH(C2H5)—(CH2)2CH3 | m.p. 37–46° |
| 263 | H | H | H | H | H | H | —CH2— | —COOCH2CH2OC3H7—i | oil; $n_D^{22}$: 1.5546 |
| 264 | H | H | Cl | H | H | H | —CH2— | —COO(CH2)13CH3 | m.p. 75–76° |
| 265 | H | H | H | H | H | H | —CH2— | —COOCH(C2H5)—C2H5 | m.p. 47–50° |
| 266 | H | H | H | H | H | H | —CH2— | —COO-(2-methylcyclohexyl) | m.p. 29–31° |
| 267 | H | H | Cl | H | H | H | —CH2— | —COOCH2—CH(C2H5)—C2H5 | m.p. 58–63° |
| 268 | H | H | H | H | H | H | —CH2— | —COOCH2CH2OCH2CH2OC2H5 | oil, $n_D^{22}$: 1.5489 |
| 269 | H | H | H | H | H | H | —CH2— | —COOCH2CH2O-phenyl | m.p. 80–81° |
| 270 | H | H | Cl | H | H | H | —CH2— | —COOCH(C2H5)—C2H5 | m.p. 55–80° |
| 271 | H | H | H | H | H | H | —CH2— | —COOCH(CH3)CH2CH(CH3)—CH3 | oil; $n_D^{22}$: 1.5463 |
| 272 | H | H | H | H | H | H | —CH2— | —COO(CH2)13CH3 | m.p. 35–36° |
| 273 | H | H | H | H | H | H | —CH2— | —COOCH2CH2O(CH2)3CH3 | oil; $n_D^{22}$: 1.5495 |
| 274 | H | H | Cl | H | H | H | —CH2— | —COOCH2CH2OCH2CH2OC2H5 | m.p. 42–43° |
| 275 | H | H | H | H | H | H | —CH2— | —COOCH2—CH(CH3)—C2H5 | oil; $n_D^{22}$: 1.5566 |
| 276 | H | H | Cl | H | H | H | —CH2— | —COOCH(CH3)CH2CH(CH3)—CH3 | m.p. 63–64° |
| 277 | H | H | H | H | H | H | —CH2— | —COSCH(CH3)—C2H5 | oil; $n_D^{22}$: 1.5973 |
| 278 | H | H | Cl | H | H | H | —CH2— | —COO-(2-methylcyclohexyl) | m.p. 98–101° |

TABLE 1-continued $$\text{(I)}$$

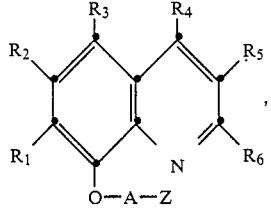

| No. | R₁ | R₂ | R₃ | R₄ | R₅ | R₆ | A | Z | Physical data |
|---|---|---|---|---|---|---|---|---|---|
| 279 | H | H | H | H | H | H | —CH₂— | —COOC(CH₃)(C₂H₅)C₂H₅ | oil; $n_D^{22}$: 1.5551 |
| 280 | H | H | H | H | H | H | —CH₂— | —COOCH₂—C(CH₃)=CH₂ | oil; $n_D^{22}$: 1.5805 |
| 281 | H | H | H | H | H | H | —CH₂— | —COOC(CH₃)₂—CH=CH₂ | oil; $n_D^{22}$: 1.5793 |
| 282 | H | H | H | H | H | H | —CH₂— | —COOCH₂CH₂OCH₂CH₂OCH₃ | oil; $n_D^{23}$: 1.5560 |
| 283 | H | H | Cl | H | H | H | —CH₂— | —COOC(CH₃)(C₂H₅)C₂H₅ | oil; $n_D^{22}$: 1.5632 |
| 284 | H | H | Cl | H | H | H | —CH₂— | —COO(CH₂)₁₀CH₃ | m.p. 70–71° |
| 285 | H | H | Cl | H | H | H | —CH₂— | —COOCH₂—CH(CH₃)—C₂H₅ | m.p. 78–79° |
| 286 | H | H | H | H | H | H | —CH₂— | —COO-(4-methylcyclohexyl) | m.p. 40–42° |
| 287 | H | H | H | H | H | H | —CH₂— | —COO(CH₂)₆CH₃ | oil; $n_D^{23}$: 1.5469 |
| 288 | H | H | H | H | H | H | —CH₂— | —COOC(CH₃)₂C₂H₅ | oil; $n_D^{22}$: 1.5581 |
| 289 | H | H | Cl | H | H | H | —CH₂— | —COOCH₂CH₂O(CH₂)₃CH₃ | m.p. 69–70° |
| 290 | H | H | Cl | H | H | H | —CH₂— | —COSCH(CH₃)C₂H₅ | m.p. 55–56° |
| 291 | H | H | Cl | H | H | H | —CH₂— | —COOC(CH₃)₂—CH=CH₂ | m.p. 83–87° |
| 292 | H | H | H | H | H | H | —CH₂— | —COSCH₃ | m.p. 41–44° |
| 293 | H | H | Cl | H | H | H | —CH₂— | —COOCH₂CH₂OCH₂CH₂OCH₃ | oil; $n_D^{23}$: 1.5633 |
| 294 | H | H | Cl | H | H | H | —CH₂— | —COSCH₃ | m.p. 89–91° |
| 295 | H | H | Cl | H | H | H | —CH₂— | —COOC(CH₃)₂C₂H₅ | m.p. 53–54° |
| 296 | H | H | H | H | H | H | —CH₂— | —COO(CH₂)₁₀CH₃ | oil; $n_D^{23}$: 1.5310 |
| 297 | H | H | Cl | H | H | H | —CH₂— | —COO(CH₂)₆CH₃ | m.p. 74–76° |
| 298 | H | H | H | H | H | H | —CH₂— | —COOCH(CH₃)—CH(CH₃)—CH₃ | oil; $n_D^{23}$: 1.554 |

TABLE 1-continued

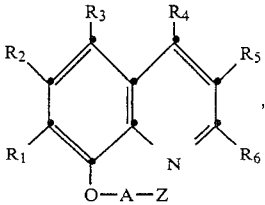

(I)

| | $R_1$ | $R_2$ | $R_3$ | $R_4$ | $R_5$ | $R_6$ | A | Z | |
|---|---|---|---|---|---|---|---|---|---|
| 299 | H | H | Cl | H | H | H | —CH$_2$— | —COO—⟨C$_6$H$_{10}$⟩—CH$_3$ (with H) | m.p. 103–105° |
| 300 | H | H | H | H | H | H | —CH$_2$— | —COSC(CH$_3$)$_3$ | oil; n$_D^{23}$: 1.5987 |
| 301 | H | H | Cl | H | H | H | —CH$_2$— | —COS(CH$_2$)$_{11}$CH$_3$ | m.p. 26–28° |
| 302 | H | H | Cl | H | H | H | —CH$_2$— | —COS(CH$_2$)$_9$CH$_3$ | m.p. 29–31° |
| 303 | H | H | Cl | H | H | H | —CH$_2$— | —COO(CH$_2$)$_9$CH$_3$ | m.p. 73–74° |
| 304 | H | H | H | H | H | H | —CH$_2$— | —COOCH(CH$_3$)(CH$_2$)$_4$CH$_3$ | oil; n$_D^{23}$: 1.5433 |
| 305 | H | H | Cl | H | H | H | —CH$_2$— | —COOCH(C$_3$H$_7$-n)—C≡CH | m.p. 81–82° |
| 306 | H | H | H | H | H | H | —CH$_2$— | —COOCH(C$_5$H$_{11}$-n)—CH=CH$_2$ | oil; n$_D^{23}$: 1.5472 |
| 307 | H | H | Cl | H | H | H | —CH$_2$— | —COOCH(CH$_3$)—CH(CH$_3$)—CH$_3$ | m.p. 70–74° |
| 308 | H | H | Cl | H | H | H | —CH$_2$— | —COSC(CH$_3$)$_3$ | oil; n$_D^{22}$: 1.5996 |
| 309 | H | H | H | H | H | H | —CH$_2$— | —COOCH(CH$_3$)—C≡CH | oil; n$_D^{23}$: 1.5837 |
| 310 | H | H | H | H | H | H | —CH$_2$— | —COS(CH$_2$)$_{11}$CH$_3$ | oil; n$_D^{23}$: 1.5523 |
| 311 | H | H | H | H | H | H | —CH$_2$— | —COOCH$_2$—C(CH$_3$)$_3$ | oil; n$_D^{22}$: 1.5524 |
| 312 | H | H | H | H | H | H | —CH$_2$— | —COSC$_2$H$_5$ | oil; n$_D^{23}$: 1.6310 |
| 313 | H | H | Cl | H | H | H | —CH$_2$— | —COOCH$_2$—C(CH$_3$)$_3$ | m.p. 76–81° |
| 314 | H | H | Cl | H | H | H | —CH$_2$— | —COSC$_3$H$_7$-n | oil; n$_D^{22}$: 1.6136 |
| 315 | H | H | H | H | H | H | —CH$_2$— | —COO(CH$_2$)$_9$CH$_3$ | oil; n$_D^{22}$: 1.5308 |
| 316 | H | H | Cl | H | H | H | —CH$_2$— | —COOCH(CH$_3$)(CH$_2$)$_4$CH$_3$ | m.p. 65–67° |
| 317 | H | H | H | H | H | H | —CH$_2$— | —COO(CH$_2$)$_2$CH(CH$_3$)—CH$_3$ | oil; n$_D^{23}$: 1.5568 |
| 318 | H | H | H | H | H | H | —CH$_2$— | —COOCH(C$_2$H$_5$)(CH$_2$)$_3$CH$_3$ | oil; n$_D^{23}$: 1.5454 |

TABLE 1-continued

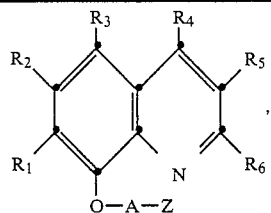

(I)

| | $R_1$ | $R_2$ | $R_3$ | $R_4$ | $R_5$ | $R_6$ | A | Z | |
|---|---|---|---|---|---|---|---|---|---|
| 319 | H | H | Cl | H | H | H | —CH$_2$— | —COO(CH$_2$)$_8$CH$_3$ | m.p. 78–79° |
| 320 | H | H | H | H | H | H | —CH$_2$— | —COSCH$_2$CH(CH$_3$)CH$_3$ | oil; $n_D^{23}$: 1.6049 |
| 321 | H | H | Cl | H | H | H | —CH$_2$— | —COSC$_2$H$_5$ | m.p. 55–57° |
| 322 | H | H | H | H | H | H | —CH$_2$— | —COO(CH$_2$)$_8$CH$_3$ | oil; $n_D^{24}$: 1.5436 |
| 323 | H | H | Cl | H | H | H | —CH$_2$— | —COOCH$_2$—CH(C$_2$H$_5$)(CH$_2$)$_3$CH$_3$ | m.p. 45–47° |
| 324 | H | H | Cl | H | H | H | —CH$_2$— | —COSCH$_2$CH(CH$_3$)—CH$_3$ | oil; $n_D^{23}$: 1.6045 |
| 325 | H | H | H | H | H | H | —CH$_2$— | —COS(CH$_2$)$_9$CH$_3$ | oil; $n_D^{23}$: 1.5630 |
| 326 | H | H | Cl | H | H | H | —CH$_2$— | —COO(CH$_2$)$_2$CH(CH$_3$)—CH$_3$ | m.p. 72–74° |
| 327 | H | H | Cl | H | H | H | —CH$_2$— | —COOCH(C$_2$H$_5$)(CH$_2$)$_3$CH$_3$ | oil; $n_D^{22}$: 1.5542 |
| 328 | H | H | H | H | H | H | —CH$_2$— | —COO(CH$_2$)$_5$CH$_3$ | oil; $n_D^{22}$: 1.5512 |
| 329 | H | H | H | H | H | H | —CH$_2$— | —COOCH(C$_3$H$_7$-n)(CH$_2$)$_2$CH$_3$ | m.p. 48–50° |
| 330 | H | H | H | H | H | H | —CH$_2$— | —COS(CH$_2$)$_4$CH$_3$ | oil; $n_D^{22}$: 1.5937 |
| 331 | H | H | H | H | H | H | —CH$_2$— | COSC$_3$H$_7$—i | oil; $n_D^{23}$: 1.5821 |
| 332 | H | H | H | H | H | H | —CH$_2$— | —COOCH$_2$CH(C$_2$H$_5$)—(CH$_2$)$_3$CH$_3$ | oil; $n_D^{22}$: 1.5395 |
| 333 | H | H | Cl | H | H | H | —CH$_2$— | —COOCH(C$_3$H$_7$-n)(CH$_2$)$_2$CH$_3$ | m.p. 55–57° |
| 334 | H | H | Cl | H | H | H | —CH$_2$— | —COS(CH$_2$)$_5$CH$_3$ | oil; $n_D^{22}$: 1.5882 |
| 335 | H | H | Cl | H | H | H | —CH$_2$— | —COS(CH$_2$)$_4$CH$_3$ | oil; $n_D^{23}$: 1.5990 |
| 336 | H | H | Cl | H | H | H | —CH$_2$— | —COO(CH$_2$)$_5$CH$_3$ | m.p. 71–72° |
| 337 | H | H | Cl | H | H | H | —CH$_2$— | —COSC$_3$H$_7$—i | m.p. 62–64° |
| 338 | H | H | Cl | H | H | H | —CH$_2$— | —COOCH(C$_2$H$_5$)—CH$_2$CH(CH$_3$)C$_2$H$_5$ | m.p. 25–29° |
| 339 | H | H | H | H | H | H | —CH$_2$— | —COOCH(C$_3$H$_7$-i)—C$_3$H$_7$—i | oil; $n_D^{22}$: 1.5468 |
| 340 | H | H | H | H | H | H | —CH$_2$— | —COOCH(CH$_3$)—(CH$_2$)$_3$CH$_3$ | oil; $n_D^{23}$: 1.5531 |
| 341 | H | H | Cl | H | H | H | —CH$_2$— | —COOCH(C$_2$H$_{11}$-n)—CH=CH$_2$ | oil; $n_D^{23}$: 1.5579 |
| 342 | H | H | H | H | H | H | —CH$_2$— | —COOCH(C$_2$H$_5$)—(CH$_2$)$_2$CH$_3$ | m.p. 42–44° |
| 343 | H | H | H | H | H | H | —CH$_2$— | —COSC$_3$H$_7$—n | oil; $n_D^{22}$: 1.6108 |

TABLE 1-continued

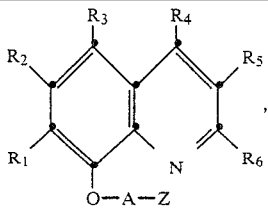
(I)

| # | R1 | R2 | R3 | R4 | R5 | R6 | A | Z | phys. data |
|---|----|----|----|----|----|----|---|---|------------|
| 344 | H | H | Cl | H | H | H | —CH₂— | —COOCH(CH₃)—(CH₂)₃CH₃ | m.p. 68–71° |
| 345 | H | H | H | H | H | H | —CH₂— | —COOCH(C₂H₅)CH₂CH(CH₃)C₂H₅ | oil; $n_D^{23}$: 1.5472 |
| 346 | H | H | Cl | H | H | H | —CH₂— | —COOCH(C₃H₇-i)—C₃H₇-i | m.p. 88–89° |
| 347 | H | H | H | H | H | H | —CH₂— | —COS(CH₂)₅CH₃ | oil; $n_D^{22}$: 1.5804 |
| 348 | H | H | H | H | H | H | —CH₂— | —COO(CH₂)₉—CH=CH₂ | oil; $n_D^{22}$: 1.5386 |
| 349 | H | H | H | H | H | H | —CH₂— | —COOCH(C₃H₇-n)—C≡CH | oil; $n_D^{22}$: 1.5659 |
| 350 | H | H | Cl | H | H | H | —CH₂— | —COOCH(CH₃)—C≡CH | m.p. 97–100° |
| 351 | H | H | H | H | H | H | —CH₂— | —COOC(CH₃)(C₂H₅)—C≡CH | oil; $n_D^{22}$: 1.5688 |
| 352 | H | H | Cl | H | H | H | —CH₂— | —COO(CH₂)₉—CH=CH₂ | m.p. 66–67° |
| 353 | H | H | Cl | H | H | H | —CH₂— | —COO—C(CH₃)₂—C≡CH | m.p. 76–81° |
| 354 | H | H | H | H | H | H | —CH₂— | —COOC(CH₃)₂—C≡CH | oil; $n_D^{23}$: 1.5740 |
| 355 | H | H | Cl | H | H | H | —CH₂— | —COOC(CH₃)(C₂H₅)—C≡CH | m.p. 78–79° |
| 356 | H | H | Cl | H | H | H | —CH₂— | —COO—CH(CH₃)—CH(CH₃)—C₂H₅ | m.p. 71–73° |
| 357 | H | H | Cl | H | H | H | —CH₂— | —COO—CH(CH₃)—(CH₂)₄CH₃ | m.p. 65–67° |

The compounds of formula I can be prepared by methods which are known per se, for example those described in European patent publications Nos. 86 750 and 94 349, or by methods similar to known ones.

The quinoline derivatives of formula I are most suited to protecting cultivated plants from the harmful effects of herbicidal derivatives of (4,5-dihydro-4-oxo-1H-imidazol-2-yl)benzoic acid, (4,5-dihydro-4-oxo-1H-imidazol-2-yl)nicotinic acid and (4,5-dihydro-4-oxo-1H-imidazol-2-yl)quinolinecarboxylic acid. These derivatives correspond to the formula II

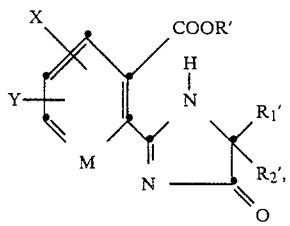
(II)

wherein R' is hydrogen, $C_1$-$C_4$alkyl, the ammonium cation or an organic ammonium cation, $R_1'$ is $C_1$-$C_4$alkyl, $R_2'$ is $C_1$-$C_4$alkyl or $C_3$-$C_6$cycloalkyl, or $R_1'$ and $R_2'$ together are $C_4$alkylene or $C_5$alkylene, M is the structural unit =CH— or =N—, X and Y are each independently of the other hydrogen, $C_1$-$C_4$alkyl or halogen or, if M is =N—, are additionally the structural unit —$C(X_1)$=$C(X_2)$—$C(X_3)$=$C(X_4)$—, wherein $X_1$, $X_2$, $X_3$ and $X_4$ are hydrogen or one or two of $X_1$, $X_2$, $X_3$ and $X_4$ are $C_1$-$C_4$alkyl and the others are hydrogen.

In the compounds of formula II, $C_1$-$C_4$alkyl will be understood to mean methyl, ethyl, n-propyl, isopropyl, n-butyl, sec-butyl, tert-butyl and isobutyl.

By organic ammonium cation is meant an ammonium cation in which one to four hydrogen atoms are replaced by an organic radical. Suitable organic radicals are preferably aliphatic radicals, most preferably those containing 1 to 20 carbon atoms. Examples of such organic ammonium cations are: monoalkylammonium, dialkylammonium, trialkylammonium, tetraalkylammonium, monoalkenylammonium, dialkenylammonium, trialkenylammonium, monoalkinylammonium, dialkinylammonium, trialkinylammonium, monoalkanolammonium, dialkanolammonium, trialkanolammonium, $C_3$-$C_6$-cycloalkylammonium, piperidinium, morpholinium, pyrrolidinium, benzylammonium and equivalents thereof.

In the compounds of formula II, halogen denotes fluorine, chlorine, bromine and iodine, preferably chlorine and bromine.

Herbicidally active compounds of formula II are described for example in U.S. Pat. No. 4,188,487 and in European patent application No. 41.623.

Especially noteworthy is the protective action of quinoline derivatives of formula I against those herbicides of formula II in which R' is hydrogen, methyl, the ammonium cation or an organic ammonium cation, $R_1'$ is methyl and $R_2'$ is isopropyl, and M, X and Y are as defined for formula II; and, in particular, against those herbicides of formula II, wherein R' is methyl, $R_1'$ is methyl, $R_2'$ is isopropyl, X is hydrogen and Y is 4- or 5-methyl, and M is the structural unit =CH—; as well as against 2-[4,5-dihydro-5-methyl-(1-methylethyl)-4-oxo-1H-imidazol-2-yl]nicotinic acid and, most particularly, 2-[4,5-dihydro-5-methyl-(1-methylethyl)-4-oxo-1H-imidazol-2-yl]-3-quinolinecarboxylic acid, and 2-[4,5-dihydro-5-methyl-(1-methylethyl-4-oxo-1H-imidazol-2-yl]-5-ethyl nicotinic acid.

Cultivated plants which can be protected by quinoline derivatives of formula I from injury caused by herbicides of formula II are, in particular, those plants that are important in the food and textile sectors, for example, cotton, sugar beet, sugar cane and, in particular, sorghum, maize, rice and other cereals (wheat, rye, barley and oats).

A suitable method of protecting cultivated plants using compounds of formula I comprises treating said plants, parts thereof or areas of soil intended for the cultivation of said plants, before or after planting, with a compound of formula I or with a composition that contains such a compound. The treatment can be effected before, simultaneously with or after the application of the herbicide of formula II. Suitable parts of plants are in particular those that are capable of plant propagation, for example seeds, fruit, stems and cuttings as well as roots, tubers and rhizomes.

The invention also relates to a method of selectively controlling weeds in crops of cultivated plants, which comprises treating said crops, parts of cultivated plants or crop areas with a herbicide of formula II and a compound of formula I or with a composition that contains a combination of such a combination of such a herbicide and a compound of formula I.

The weeds to be controlled can be both monocotyledonous and dicotyledonous weeds.

Suitable cultivated plants or parts thereof are, for example, those mentioned above. Crop areas will be understood as meaning the areas of soil already planted with the cultivated plants or with crop seeds of said plants, and the areas of soil intended for the cultivation of said plants.

The ratio of the concentration of safener to be applied to that of herbicide will depend substantially on the mode of application. For a field treatment, which is made either using a tank mixture with a combination of safener and herbicide or by separate application of safener and herbicide, the ratio of safener to herbicide will normally be in the range from 1:100 to 10:1, preferably from 1:5 to 8:1 and, most preferably, from 1:1. However, for seed dressing, substantially lower amounts of safener are required in proportion to the concentration of herbicide per hectare of crop area.

For a field treatment, 0.1 to 10 kg, preferably 0.,5 to 2 kg, of safener per hectare will usually be applied.

For seed dressing, 0.01 to 10 g, preferably 0.05 to 1 g, of safener per hectare will normally be applied. If the safener is applied in liquid form shortly before sowing by seed soaking, then it is convenient to use safener solutions that contain the active ingredient in a concentration of 1 to 10,000 ppm, preferably from 100 to 1000 ppm.

For application, the compounds of formula, or combinations of compounds of formula I with the herbicides to be antagonised, are conveniently used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I or a combination of compound of formula I with the herbicide it is desired to antagonise and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monomethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorptive polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, and, where appropriate, also of the herbicide which it is desired to antagonise, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylenepolyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979; Helmut Stache, "Tensid-Taschenbuch", Carl Hanser Verlag, Munich/Vienna, 1981.

The agrochemical compositions usually contain 0.1 to 99% by weight, preferably 0.1 to 95% by weight, of a compound of the formula I, or of a mixture of safener and herbicide, 1 to 99% by weight of a solid or liquid adjuvant, and 0 to 25% by weight, preferably 0.1 to 25% by weight, of a surfactant.

Whereas commercial products are preferably formulated as concentrates, the end user will normally employ dilute formulations.

The compositions may also contain further ingredients such as stabilisers, antifoams, viscosity regulators, binders, tactifiers as well as fertilisers or other active ingredients in order to obtain special effects.

Various methods are suitable for using compounds of formula I, or compositions containing them, for protecting cultivated plants from injury caused by herbicides of formula II, for example:

(i) Seed dressing

Dressing the seeds with a wettable powder formulation of a compound of formula I by shaking in a vessel until a uniform coating is obtained on the surface of the seeds (dry dressing). About 1 to 500 g of compound of formula I (4 g to 2 kg of wettable powder) are used per 100 kg of seeds.

(b) Dressing the seeds by immersing them in a emusifiable concentrate of a compound of formula I in accordance with the procedure of method (a) (wet dressing).

(c) Dressing the seeds by immersing them for 1 to 72 hours in a mixture containing 50–3200 ppm of compound of formula I and, if desired, subsequently drying the seeds (immersion dressing).

It will be appreciated that dressing the seeds or treating the germinated seedlings are the preferred methods of application, because the treatment is directed entirely to the target crop. Normally 1 to 500 g, preferably 5 to 250 g, of safener are used per 100 g of seeds, although deviations above and below these concentrations (repeat dressings), are possible depending on the method employed, which also permits the addition of other active compounds or micronutrients.

(ii) Application from a tank mixture

A liquid formulation of a mixture of safener and herbicide (reciprocal ratio from 10:1 to 1:10) is used, with the concentration of herbicide being from 0.1 to 10 kg per hectare. Such a tank mixture is applied preferably before or immediately after sowing and is incorporated to a depth of 5 to 10 cm int the as yet unsown soil.

(iii) Application to the seed furrow

The safener is applied to the open sown seed furrow as emulsifiable concentrate, wettable powder or in granular form, and then the herbicide is applied preemergence in the normal manner after covering the furrow.

(iv) Controlled release of active ingredient

A solution of a compound of formula I is applied to mineral granulate carriers or polymerised granulates (urea/formaldehyde) and allowed to dry. If desired, a coating may be applied (coated granules), which permits controlled release of the active ingredient over a specific period of time.

Formulation Examples for liquid active ingredients of the formula I (throughout, percentages are by weight)

| 1. Emulsifiable concentrates | (a) | (b) | (c) |
| --- | --- | --- | --- |
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2. Solutions | (a) | (b) | (c) | (d) |
| --- | --- | --- | --- | --- |
| a compound of Table 1 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| 3. Granulates | (a) | (b) |
| --- | --- | --- |
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
| --- | --- | --- |
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| 5. Wettable powders | (a) | (b) | (c) |
| --- | --- | --- | --- |
| a compound of Table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 6. Emulsifiable concentrate | |
| --- | --- |
| a compound of Table 1 | 10% |
| octylphenol polyethlene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
| --- | --- | --- |
| a compound of Table 1 | 5% | 8% |
| talcum | 95% | — |
| kaolin | — | 92% |

Ready-for-use dusts are obtained by mixing the active ingredient with the carriers, and grinding the mixture in a suitable mill.

| 8. Extruder granulate | |
| --- | --- |
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| 9. Coated granulate | (a) | (b) |
| --- | --- | --- |
| a compound of Table 1 | 3% | 5% |
| polyethylene glycol 200 | 3% | 3% |
| kaolin | 94% | 92% |

The finely ground active ingredient is uniformly applied, in a mixer, to the kaolin moistened with polyethylene glycol. Non-dusty coated granulates are obtained in this manner.

| 10. Suspension concentrate | |
| --- | --- |
| a compound of Table 1 | 40% |
| ethylene glycol | 10% |
| nonylphenol polyethylene glycol (15 moles of ethylene oxide) | 6% |

| 10. Suspension concentrate | |
|---|---|
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the aduvants, giving a suspension concentrate from which suspensions of any desired concentration can be obtained by dilution with water. Formulation assistants which increase the adhesion of the active ingredient to the plant, e.g. mineral or vegetable oils, act very advantageously in foliar application.

| 11. Emulsifiable concentrates | (a) | (b) | (c) |
|---|---|---|---|
| 1:1 mixture of a safener of Table 1 and a herbicide of formula II | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 12. Emulsifiable concentrates | (a) | (b) | (c) |
|---|---|---|---|
| 1:3 mixture of a safener of Table 1 and a herbicide of formula II | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 13. Emulsifiable concentrates | (a) | (b) | (c) |
|---|---|---|---|
| 2:1 mixture of a safener of Table 1 and a herbicide of formula II | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 14. Emulsifiable concentrates | (a) | (b) | (c) |
|---|---|---|---|
| 1:1 mixture of a safener of Table 1 and 2-[4,5-dihydro-5-methyl-5-(1-methyl-ethyl)-4-oxo-1H—imidazol-2-yl]-3-quinolinecarboxylic acid | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 15. Emulsifiable concentrates | (a) | (b) | (c) |
|---|---|---|---|
| 1:3 mixture of a safener of Table 1 and 2-[4,5-dihydro-5-methyl-5-(1-methyl-ethyl)-4-oxo-1H—imidazol-2-yl]-3-quinolinecarboxylic acid | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 16. Solutions | (a) | (b) | (c) | (d) |
|---|---|---|---|---|
| 1:4 mixture of a safener of Table 1 and a herbicide of formula II | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 17. Solutions | (a) | (b) | (c) | (d) |
|---|---|---|---|---|
| 5:2 mixture of a safener of Table 1 and a herbicide of formula II | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 18. Solutions | (a) | (b) | (c) | (d) |
|---|---|---|---|---|
| 1:1 mixture of a safener of Table 1 and a herbicide of formula II | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 19. Solutions | (a) | (b) | (c) | (d) |
|---|---|---|---|---|
| 1:1 mixture of a safener of Table 1 and 2-[4,5-dihydro-5-methyl-5-(1-methyl-ethyl-)4-oxo-1H—imidazol-2-yl]-3-quinolinecarboxylic acid | 80% | 10% | 5% | 95% |

-continued

| 19. Solutions | (a) | (b) | (c) | (d) |
|---|---|---|---|---|
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 20. Solutions | (a) | (b) | (c) | (d) |
|---|---|---|---|---|
| 1:4 mixture of a safener of Table 1 and a herbicide of formula II | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 21. Granulates | (a) | (b) |
|---|---|---|
| 1:1 mixture of a safener of Table 1 and a herbicide of formula II | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 22. Granulates | (a) | (b) |
|---|---|---|
| 1:1 mixture of a safener of Table 1 2-[4,5-dihydro-5-methyl-5-(1-methyl-ethyl-)4-oxo-1H—imidazol-2-yl]-3-quinolinecarboxylic acid | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 23. Dusts | (a) | (b) |
|---|---|---|
| 1:1 mixture of a safener of Table 1 and a herbicide of formula II | 2% | 5% |
| highly dispersed silicic acid | 1% | 5% |
| talcum | 97% | — |
| kaolin | — | 90% |

Ready-for-use dusts are obtained by intimately mixing the carriers with the acitve ingredient.

Formulation examples for solid active ingredients of the formula I (throughout, percentages are by weight)

| 24. Wettable powders | (a) | (b) | (c) |
|---|---|---|---|
| 1:1 mixture of a safener of Table 1 and a herbicide of formula II | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |

Formulation examples for solid active ingredients of the formula I (throughout, percentages are by weight)

| 24. Wettable powders | (a) | (b) | (c) |
|---|---|---|---|
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 25. Wettable powders | (a) | (b) | (c) |
|---|---|---|---|
| 1:4 mixture of a safener of Table 1 and a herbicide of formula II | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly ground in a suitable mill, affording wettable powders which can be diluted with water to give suspensions of the desired concentration.

| 26. Wettable powders | (a) | (b) | (c) |
|---|---|---|---|
| 3:1 mixture of a safener of Table 1 and a herbicide of formula II | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 27. Emulsifiable concentrate | |
|---|---|
| 1:1 mixture of a safener of Table 1 and a herbicide of formula II | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 28. Emulsifiable concentrate | |
|---|---|
| 5:2 mixture of a safener of Table 1 and a herbicide of formula II | 10% |
| octylphenol polyethlene glycol ether (4–5 moles of ethylene oxide) | 3% |
| calcium dodecylbenzenesulfonate | 3% |

| 28. Emulsifiable concentrate | |
|---|---|
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 29. Emulsifiable concentrate | |
|---|---|
| 1:4 mixture of a safener of Table 1 and a herbicide of formula II | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 30. Dusts | (a) | (b) |
|---|---|---|
| 1:1 mixture of a safener of Table 1 and a herbicide of formula II | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 31. Extruder granulate | |
|---|---|
| 1:1 mixture of a safener of Table 1 and a herbicide of formula II | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a strem of air.

| 32. Coated granulate | (a) | (b) |
|---|---|---|
| 1:1 mixture of a safener of Table 1 and a herbicide of formula II | 3% | 5% |
| polyethylene glycol 200 | 3% | 3% |
| kaolin | 94% | 92% |

The finely ground active ingredient is uniformly applied, in a mixer, to the kaolin moistened with polyethlene glycol. Non-dusty coated granulates are obtained in this manner.

| 33. Suspension concentrate | |
|---|---|
| 1:1 mixture of a safener of Table 1 and a herbicide of formula II | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution silicone oil in the form of a 75% | 0.2% |
| aqueous emulsion | 0.8% |
| water | 32% |

The finely ground active ingredient is intimately mixed with the aduvants, giving a suspension concentrate from which suspensions of any desired concentration can be obtained by dilution with water. Formulation assistants which increase the adhesion of the active ingredient to the plant, e.g. mineral or vegetable oils, act very advantageously in foliar application.

| 34. Suspension concentrate | |
|---|---|
| 1:4 mixture of a safener of Table 1 and a herbicide of formula II | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution silicone oil in the form of a 75% | 0.2% |
| aqueous emulsion | 0.8% |
| water | 32% |

The finely ground active ingredient is intimately mixed with the aduvants, giving a suspension concentrate from which suspensions of any desired concentration can be obtained by dilution with water. Formulation assistants which increase the adhesion of the active ingredient to the plant, e.g. mineral or vegetable oils, act very advantageously in foliar application.

| 35. Suspension concentrate | |
|---|---|
| 3:1 mixture of a safener of Table 1 and a herbicide of formula II | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution silicone oil in the form of a 75% | 0.2% |
| aqueous emulsion | 0.8% |
| water | 32% |

The finely ground active ingredient is intimately mixed with the aduvants, giving a suspension concentrate from which suspensions of any desired concentration can be obtained by dilution with water.

BIOLOGICAL EXAMPLES

Example 36: Dressing of wheat seeds with preemergence application of the herbicide Wheat seeds of the "Besso" variety are put into a glass container with the safener to be tested, viz. 0-methoxycarbonyl-2-(8-quinolinoxy)acetamidoxime (compound 11). Seeds and safener are thoroughly mixed by shaking and rotation. Plastic pots having a diameter of 11 cm at the top are filled with 0.5 l of sandy loam and the dressed seeds are sown therein. After covering the seeds with soil, the herbicide, viz. 2-[4,5-dihydro-5-methyl-5-(1-methylethyl)-4-oxo-1H-imidazol-2-yl]-3-quinolinecarboxylic acid, is sprayed onto the surface of the soil. Percentage evaluation of the protective action of the safener is made 21 days after application of the herbicide. The plants treated with the herbicide alone and the completely untreated controls serve as reference for the evaluation. The results are reported in Table 2.

TABLE 2

| Safener g a.i./kg seeds | Herbicide kg a.i./ha | Relative protective action in % |
|---|---|---|
| 4 | 0.2 | 0 |
| 4 | 0.1 | 62.5 |
| 4 | 0.05 | 75 |
| 4 | 0.025 | 62.5 |
| 4 | 0.0125 | 0 |
| 2 | 0.2 | 12.5 |
| 2 | 0.1 | 37.5 |
| 2 | 0.05 | 75 |
| 2 | 0.025 | 62.5 |
| 2 | 0.0125 | 12.5 |
| 1 | 0.2 | 12.5 |
| 1 | 0.1 | 37.5 |
| 1 | 0.05 | 62.5 |
| 1 | 0.025 | 62.5 |
| 1 | 0.0125 | 25 |

EXAMPLE 37: Dressing of barley seeds. Presowing treatment with herbicide

Barley seeds of the "Cornel" variety are put into a glass container with the safener to be tested, viz. 5-chloro-8-(cyanomethoxy)quinoline (compound 7) or O-methoxycarbonyl-2-(8-quinolinoxy)acetamidoxime (compound 11). Seeds and safener are thoroughly mixed by shaking and rotation. Plastic containers measuring 25×17×12 cm are filled with sandy loam and the herbicide, viz. 2-[4,5-dihydro-5-methyl-5-(1-methylethyl)-4-oxo-1H-imidazol-2-yl]-3-quinolinecarboxylic acid, is sprayed onto the surface of the soil and then incorporated into the soil. The seeds are then sown in the pretreated soil. Percentage evaluation of the protective action is made 21 days after application of the herbicide. The plants treated with herbicide alone and the completely untreated controls serve as reference for the evaluation. The results are reported in the Table 3.

TABLE 3

| Safener compound No. | Herbicide kg a.i./ha | Safener g a.i./kg seeds | Relative protective action in % |
|---|---|---|---|
|  | 0.1 | 2 | 12.5 |
| 7 | 0.05 | 2 | 0 |
|  | 0.025 | 2 | 0 |
|  | 0.1 | 1 | 25 |
| 7 | 0.05 | 1 | 12.5 |
|  | 0.025 | 1 | 0 |
|  | 0.1 | 0.5 | 50 |
| 7 | 0.05 | 0.5 | 25 |
|  | 0.025 | 0.5 | 0 |
|  | 0.1 | 0.25 | 50 |
| 7 | 0.05 | 0.25 | 37.5 |
|  | 0.025 | 0.25 | 12.5 |
|  | 0.1 | 2 | 62.5 |
| 11 | 0.05 | 2 | 62.5 |
|  | 0.025 | 2 | 37.5 |
|  | 0.1 | 1 | 62.5 |
| 11 | 0.05 | 1 | 62.5 |
|  | 0.025 | 1 | 37.5 |
|  | 0.1 | 0.5 | 62.5 |
| 11 | 0.05 | 0.5 | 62.5 |
|  | 0.025 | 0.5 | 37.5 |
|  | 0.1 | 0.25 | 50 |
| 11 | 0.05 | 0.25 | 50 |
|  | 0.025 | 0.25 | 37.5 |

EXAMPLE 38: Dressing of wheat seeds. Presowing treatment with herbicide

Wheat seeds of the "Besso" variety are put into a glass container with the safener to be tested, viz. 5-chloro-8-(cyanomethoxy)quinoline (compound 7) or O-methoxycarbonyl-2-(8-quinolinoxy)acetamidoxime (compound 11). Seeds and safener are thoroughly mixed by shaking and rotation. Plastic containers measuring 25×17×12 cm are filled with sandy loam and the herbicide, viz. 2-[4,5-dihydro-5-methyl-5-(1-methylethyl)-4-oxo-1H-imidazol-2-yl]-3-quinolinecarboxylic acid, is sprayed onto the surface of the soil and then incorporated into the soil. The seeds are then sown in the pretreated soil. Percentage evaluation of the protective action is made 21 days after application of the herbicide. The plants treated with herbicide alone and the completely untreated controls serve as reference for the evaluation. The results are reported in Table 4.

TABLE 4

| Safener compound No. | Herbicide kg a.i./ha | Safener g a.i./kg seeds | Relative protective action in % |
|---|---|---|---|
|  | 0.1 | 2 | 50 |
| 7 | 0.05 | 2 | 12.5 |
|  | 0.025 | 2 | 0 |
|  | 0.1 | 1 | 50 |
| 7 | 0.05 | 1 | 25 |
|  | 0.025 | 1 | 0 |
|  | 0.1 | 0.5 | 62.5 |
| 7 | 0.05 | 0.5 | 25 |
|  | 0.025 | 0.5 | 0 |
|  | 0.1 | 0.25 | 62.5 |
| 7 | 0.05 | 0.25 | 25 |
|  | 0.025 | 0.25 | 0 |
|  | 0.1 | 2 | 50 |
| 11 | 0.05 | 2 | 25 |
|  | 0.025 | 2 | 0 |
|  | 0.1 | 1 | 62.5 |
| 11 | 0.05 | 1 | 37.5 |
|  | 0.025 | 1 | 12.5 |
|  | 0.1 | 0.5 | 75 |
| 11 | 0.05 | 0.5 | 37.5 |
|  | 0.025 | 0.5 | 12.5 |
|  | 0.1 | 0.25 | 75 |
| 11 | 0.05 | 0.25 | 37.5 |
|  | 0.025 | 0.25 | 12.5 |

EXAMPLE 39: Preemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. O-methoxycarbonyl-2-(8-quinolinoxy)acetamidoxime (compound 11) or n-butyl 2-(5-chloro-8-quinolinoxy)acetate (compound 125) or methylallyl 2-(5-chloro-8-quinolinoxy)acetate (compound 186), together with the herbicide, viz. 2-[4,5-dihydro-5-methyl-5-(1-methylethyl)-4-oxo-1H-imidazol-2-yl]-3-quinolinecarboxylic acid, in the ratio of 1:1, is applied preemergence. Percentage evaluation of the protective action is made 10 days after application. The plants treated with the herbicide alone as well as the completely untreated controls serve as reference for the evaluation. The results are reported in Table 5.

TABLE 5

| Safener Compound No. | Safener kg a.i./ha | Herbicide kg a.i./ha | Relative protective action in % |
|---|---|---|---|
|  | 0.1 | 0.1 | 37.5 |
| 11 | 0.05 | 0.05 | 37.5 |
|  | 0.025 | 0.025 | 12.5 |
|  | 0.1 | 0.1 | 12.5 |
| 125 | 0.05 | 0.05 | 25 |
|  | 0.025 | 0.025 | 12.5 |
|  | 0.1 | 0.1 | 12.5 |
| 186 | 0.05 | 0.05 | 25 |
|  | 0.025 | 0.025 | 0 |

EXAMPLE 40: Preemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. O-methoxycarbonyl-2-(8-quinolinoxy)acetamidoxime (compound 11) or n-butyl 2-(5-chloro-8-quinolinoxy)acetate (compound 125) or methylallyl 2-(5-chloro-8-quinolinoxy)acetate (compound 186), together with the herbicide, viz. 2-[4,5-dihydro-5-methyl-5-(1-methylethyl)-4-oxo-1H-imidazol-2-yl]-3-quinolinecarboxylic acid, in the ratio of 1:1, is applied preemergence. Percentage evaluation of the protective action is made 10 days after application. The plants treated with the herbicide alone as well as the completely untreated controls serve as reference for the evaluation. The results are reported in Table 6.

TABLE 6

| Safener Compound No. | Safener kg a.i./ha | Herbicide kg a.i./ha | Relative protective action in % |
|---|---|---|---|
|  | 0.1 | 0.1 | 12.5 |
| 11 | 0.05 | 0.05 | 25 |
|  | 0.025 | 0.025 | 0 |
|  | 0.1 | 0.1 | 62.5 |
| 125 | 0.05 | 0.05 | 37.5 |
|  | 0.025 | 0.025 | 12.5 |
|  | 0.1 | 0.1 | 62.5 |
| 186 | 0.05 | 0.05 | 37.5 |
|  | 0.025 | 0.025 | 0 |

EXAMPLE 41: Dressing of maize seeds with preemergence application of the herbicide Maize seeds of the "LG 5" variety are put into a glass container with the safener to be tested, viz. n-butyl 2-(5-chloro-8-quinolinoxy)acetate (compound 125). Seeds and safener are thoroughly mixed by shaking and rotation. Plastic pots having a diameter of 11 cm at the top are filled with 0.5 l of sandy loam and the dressed seeds are sown therein. After covering the seeds with soil, the herbicide, viz. 2-[4,5-dihydro-5-methyl-5-(1-methylethyl)-4-oxo-1H-imidazol-2-yl]-3-quinolinecarboxylic acid, is applied preemergence. Percentage evaluation of the protective action of the safener is made 20 days after application of the herbicide. The plants treated with the herbicide alone and the completely untreated controls serve as reference for the evaluation. The results are reported in Table 7.

TABLE 7

| Safener g a.i./kg seeds | Herbicide kg a.i./ha | Relative protective action in % |
|---|---|---|
| 2 | 0.05 | 25 |
| 1 | 0.05 | 25 |
| 0.5 | 0.05 | 12.5 |
| 2 | 0.025 | 0 |
| 1 | 0.025 | 12.5 |
| 0.5 | 0.025 | 0 |

EXAMPLE 42: Postemergence test with safener and herbicide as tank mixture

Wheat seeds of the "Besso" variety are sown in a greenhouse in plastic pots (diameter at the top 11 cm) containing 0.5 l of sandy loam. A tank mixture of the safener to be tested, viz. O-methoxycarbonyl-2-(8-quinolinoxy)acetamidoxime (compound 11) or n-butyl 2-(5-chloro-8-quinolinoxy)acetate (compound 125) or methylallyl 2-(5-chloro-8-quinolinoxy)acetate (compound 186), together with the herbicide, viz. 2-[4,5-dihydro-5-methyl-5-(1-methylethyl)-4-oxo-1H-imidazol-2-yl]-3-quinolinecarboxylic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 8.

TABLE 8

| Safener Compound No. | Safener g a.i./ha | Herbicide g a.i./ha | Relative protective action in % |
|---|---|---|---|
|  | 100 | 100 | 50 |
|  | 50 |  | 40 |
|  | 25 |  | 30 |
| 11 | 12.5 |  | 40 |
|  | 50 | 50 | 50 |
|  | 25 |  | 50 |
|  | 12.5 |  | 45 |
|  | 6.25 |  | 35 |
|  | 200 |  | 95 |
|  | 100 | 200 | 80 |
|  | 50 |  | 80 |
|  | 25 |  | 50 |
|  | 100 |  | 80 |
| 125 | 50 | 100 | 85 |
|  | 25 |  | 85 |
|  | 12.5 |  | 70 |
|  | 50 |  | 40 |
|  | 25 | 50 | 45 |
|  | 12.5 |  | 40 |
|  | 6.25 |  | 40 |
|  | 200 |  | 75 |
|  | 100 | 200 | 80 |
|  | 50 |  | 70 |
|  | 25 |  | 50 |
|  | 100 | 100 | 85 |
| 186 | 50 |  | 85 |
|  | 25 |  | 85 |
|  | 12.5 |  | 55 |
|  | 50 | 50 | 50 |
|  | 25 |  | 50 |
|  | 12.5 |  | 50 |
|  | 6.25 |  | 50 |

EXAMPLE 43: Dressing of maize seeds with preemergence application of the herbicide Maize seeds of the "LG 5" variety are put into a glass container with the safener to be tested, viz. n-butyl 2-(5-chloro-8-quinolinoxy)acetate (compound 125).

Seeds and safener are thoroughly mixed by shaking and rotation. Plastic pots having a diameter of 11 cm at the top are filled with 0.5 l of sandy loam and the dressed seeds are sown therein. After covering the seeds with soil, the herbicide, viz. 2-[4,5-dihydro-5-methyl-5-(1-methylethyl)-4-oxo-1H-imidazol-2-yl]-5-ethyl nicotinic acid, is applied preemergence. Percentage evaluation of the protective action of the safener is made 21 days after application of the herbicide. The plants treated with the herbicide alone and the completely untreated controls serve as reference for the evaluation. The results are reported in Table 9.

TABLE 9

| Safener g a.i./kg seeds | Herbicide kg a.i./ha | Relative protective action in % |
|---|---|---|
| 2 | 0.200 | 20 |
| 1 | 0.200 | 20 |
| 0.5 | 0.200 | 10 |
| 2 | 0.100 | 35 |
| 1 | 0.100 | 45 |
| 0.5 | 0.100 | 5 |

EXAMPLE 44: Postemergence test with safener and herbicide as tank mixture

Wheat seeds of the "Besso" variety are sown in a greenhouse in plastic pots (diameter at the top 11 cm) containing 0.5 l of sandy loam. A tank mixture of the safener to be tested, viz. n-butyl 2-(5-chloro-8-quinolinoxy)acetate (compound 125) or methylallyl 2-(5-chloro-8-quinolinoxy)acetate (compound 186), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 10.

TABLE 10

| Safener Compound No. | Safener g a.i./kg | Herbicide g a.i./ha | Relative protective action in % |
|---|---|---|---|
| 125 | 800 | 200 | 80 |
|  | 200 | 200 | 80 |
|  | 50 | 200 | 85 |
|  | 400 | 100 | 25 |
|  | 100 | 100 | 30 |
|  | 25 | 100 | 30 |
| 186 | 800 | 200 | 25 |
|  | 200 | 200 | 70 |
|  | 50 | 200 | 65 |
|  | 400 | 100 | 10 |
|  | 100 | 100 | 30 |
|  | 25 | 100 | 35 |

EXAMPLE 45: Postemergence test with safener and herbicide as tank mixture

Barley seeds of the "Cornel" variety are sown in a greenhouse in plastic pots (diameter at the top 11 cm) containing 0.5 l of sandy loam. A tank mixture of the safener to be tested, viz. n-butyl 2-(5-chloro-8-quinolinoxy)acetate (compound 125) or methylallyl 2-(5-chloro-8-quinolinoxy)acetate (compound 186), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence (three leaf stage of the plant). Percentage evaluation of the protective action is made 21 days after application. The plants treated with the herbicide alone as well as the completely untreated controls serve as reference for the evaluation. The results are reported in Table 11.

TABLE 11

| Safener Compound No. | Safener g a.i./ha | Herbicide g a.i./ha | Relative protective action in % |
|---|---|---|---|
| 125 | 800 | 200 | 55 |
|  | 200 | 200 | 55 |
|  | 50 | 200 | 30 |
|  | 400 | 100 | 30 |
|  | 100 | 100 | 30 |
|  | 25 | 100 | 20 |
| 186 | 800 | 200 | 40 |
|  | 200 | 200 | 45 |
|  | 50 | 200 | 15 |
|  | 400 | 100 | 30 |
|  | 100 | 100 | 35 |
|  | 25 | 100 | 25 |

EXAMPLE 46: Dressing of wheat seeds with postemergent application of the herbicide Wheat seeds of the "Besso" variety are put into a glass container with the safener to be tested, viz. n-butyl 2-(5-chloro-8-quinolinoxy)acetate (compound 125) or methylallyl 2-(5-chloro-8-quinolinoxy)acetate (compound 186). Seeds and safener are thoroughly mixed by shaking and rotation. Plastic pots having a diameter of 11 cm at the tope are filled with 0,5 l of sandy loam and the dressed seeds are sown therein. The herbicide, viz. 2-[4,5-dihydro-5-methyl-5-(1-methylethyl)-4-oxo-1H-imidazol-2-yl]-5-ethyl nicotinic acid in different rations is applied in postemergence process (three leaf stage of the plant). Percentage evaluation of the protecting action is made 21 days after the herbicide application. The plants treated with herbicide alone as well as the completely untreated controls serve as reference for the evaluation. The results are as reported in table 12.

TABLE 12

| Safener Compound No. | Safener g a.i./kg seeds | Herbicide g a.i./ha | Relative protective action in % |
|---|---|---|---|
| 125 | 4 | 200 | 80 |
|  | 2 | 200 | 55 |
|  | 1 | 200 | 30 |
|  | 0.5 | 200 | 10 |
|  | 4 | 100 | 70 |
|  | 2 | 100 | 75 |
|  | 1 | 100 | 80 |
|  | 0.5 | 100 | 80 |
| 186 | 1 | 200 | 55 |
|  | 0.5 | 200 | 55 |
|  | 1 | 100 | 75 |
|  | 0.5 | 100 | 80 |

EXAMPLE 47: Dressing of barley seeds with postemergent application of the herbicide Barley seeds of the "Cornel" variety are put into a glass container with the safener to be tested, viz. n-butyl 2-(5-chloro-8-quinolinoxy)acetate (compound 125) or methylallyl 2-(5-chloro-8-quinolinoxy)acetate (compound 186). Seeds and safener are thoroughly mixed by shaking and rotation. Plastic pots having a diameter of 11 cm at the tope are filled with 0,5 l of sandy loafm and the dressed seeds are sown therein. The herbicide, viz. 2-[4,5-dihydro-5-methyl-5-(1-methylethyl)-4-oxo-1H-imidazol-2-yl]-5-ethyl nicotinic acid in different rations is applied in postemergence process (three leaf stage of the plant). Percentage evaluation of the protecting action is made 21 days after the herbicide application. The plants treated with herbicide alone as well as the completely untreated controls serve as reference for the evaluation. The results are as reported in table 13.

TABLE 13

| Safener Compound No. | Safener g a.i./kg seeds | Herbicide g a.i./ha | Relative protective action in % |
|---|---|---|---|
| 125 | 4 | 200 | 45 |
| | 2 | 200 | 50 |
| | 1 | 200 | 65 |
| | 0.5 | 200 | 35 |
| | 4 | 100 | 30 |
| | 2 | 100 | 35 |
| | 1 | 100 | 35 |
| | 0.5 | 100 | 35 |
| 186 | 1 | 200 | 45 |
| | 0.5 | 200 | 50 |
| | 1 | 100 | 25 |
| | 0.5 | 100 | 25 |

EXAMPLE 48: Postemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-5-propyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 14.

TABLE 14

| Safener Compound No. | Safener g a.i./ha | Herbicide g a.i./ha | Relative protective action in % |
|---|---|---|---|
| 125 | 400 | 400 | 60 |
| | 200 | 400 | 50 |
| | 100 | 400 | 15 |
| | 200 | 200 | 65 |
| | 100 | 200 | 70 |
| | 50 | 200 | 75 |
| | 100 | 100 | 75 |
| | 50 | 100 | 75 |
| | 25 | 100 | 75 |
| 188 | 200 | 200 | 50 |
| | 100 | 200 | 60 |
| | 50 | 200 | 25 |
| | 100 | 100 | 80 |
| | 50 | 100 | 75 |
| | 25 | 100 | 70 |

EXAMPLE 49: Postemergence test with safener and herbicide as tank mixture

Barley seeds of the "Cornel" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-5-n-propyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 15.

TABLE 15

| Safener Compound No. | Safener g a.i./ha | Herbicide g a.i./ha | Relative protective action in % |
|---|---|---|---|
| 125 | 400 | 400 | 50 |
| | 200 | 400 | 50 |
| | 100 | 400 | 35 |
| | 200 | 200 | 55 |
| | 100 | 200 | 70 |
| | 100 | 100 | 45 |
| | 50 | 100 | 45 |
| | 25 | 100 | 45 |
| 188 | 200 | 200 | 35 |
| | 100 | 200 | 40 |
| | 50 | 200 | 30 |
| | 100 | 100 | 20 |
| | 50 | 100 | 25 |
| | 25 | 100 | 30 |

EXAMPLE 50: Postemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-5-(1-methylethyl)nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 16.

TABLE 16

| Safener Compound No. | Safener g a.i./ha | Herbicide g a.i./ha | Relative protective action in % |
|---|---|---|---|
| 125 | 400 | 400 | 30 |
| | 200 | 400 | 15 |
| | 100 | 400 | 15 |
| | 200 | 200 | 45 |
| | 100 | 200 | 35 |
| | 50 | 200 | 20 |
| | 100 | 100 | 65 |
| | 50 | 100 | 70 |
| | 25 | 100 | 70 |
| 188 | 200 | 200 | 20 |
| | 100 | 200 | 20 |
| | 50 | 200 | 10 |
| | 100 | 100 | 65 |
| | 50 | 100 | 50 |

TABLE 16-continued

| Safener Compound No. | Safener g a.i./ha | Herbicide g a.i./ha | Relative protective action in % |
|---|---|---|---|
| | 25 | 100 | 30 |

EXAMPLE 51: Postemergence test with safener and herbicide as tank mixture

Barley seeds of the "Cornel" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) together with the herbicide, viz. 2-[4,5-dihydro-5-methyl-5-(1-methylethyl)-4-oxo-1H-imidazol-2-yl]-5-(1-methylethyl)-nicotinic acid in different ratios is applied postemergence process (three leaf stage of the plant). Percentage evaluation of the protective action is made 21 days after application. The plants treated with the herbicide alone as well as the completely untreated controls serve as reference for the evaluation. The results are reported in Table 17.

TABLE 17

| Safener Compound No. | Safener g a.i./ha | Herbicide g a.i./ha | Relative protective action in % |
|---|---|---|---|
| | 200 | 200 | 20 |
| 125 | 100 | 200 | 25 |
| | 50 | 200 | 20 |
| | 100 | 100 | 25 |
| | 50 | 100 | 35 |
| | 25 | 100 | 35 |

EXAMPLE 52: Postemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-3-quinolinecarboxylic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 18.

TABLE 18

| Safener Compound No. | Safener g a.i./ha | Herbicide g a.i./ha | Relative protective action in % |
|---|---|---|---|
| | 400 | 400 | 80 |
| | 200 | 400 | 60 |
| | 100 | 400 | 30 |
| | 200 | 200 | 80 |
| 125 | 100 | 200 | 70 |
| | 50 | 200 | 65 |
| | 100 | 100 | 55 |
| | 50 | 100 | 60 |
| | 25 | 100 | 65 |
| | 200 | 200 | 70 |
| 188 | 100 | 200 | 35 |
| | 50 | 200 | 25 |
| | 100 | 100 | 65 |
| | 50 | 100 | 65 |
| | 25 | 100 | 60 |

EXAMPLE 53: Postemergence test with safener and herbicide as tank mixture

Wheat seeds of the "Besso" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-5-ethyl nicotinic acid, in different ratios is applied in post-emergence process (three leaf stage of the plant). Percentage evaluation of the protective action is made 21 days after application. The plants treated with the herbicide alone as well as the completely untreated controls serve as reference for the evaluation. The results are reported in Table 19.

TABLE 19

| Safener Compound No. | Safener g a.i./ha | Herbicide g a.i./ha | Relative protective action in % |
|---|---|---|---|
| | 400 | 400 | 60 |
| | 200 | 400 | 55 |
| | 100 | 400 | 50 |
| | 200 | 200 | 60 |
| 125 | 100 | 200 | 65 |
| | 50 | 200 | 80 |
| | 100 | 100 | 40 |
| | 50 | 100 | 40 |
| | 25 | 100 | 40 |
| | 400 | 400 | 50 |
| | 200 | 400 | 55 |
| | 100 | 400 | 55 |
| | 200 | 200 | 65 |
| 188 | 100 | 200 | 70 |
| | 50 | 200 | 65 |
| | 100 | 100 | 40 |
| | 50 | 100 | 40 |
| | 25 | 100 | 40 |

EXAMPLE 54: Postemergence test with safener and herbicide as tank mixture

Barley seeds of the "Cornel" variety are sown in a greenhouse in plastic pots (diameter at the top 11 cm) containing 0.5 l of sandy loam. After covering the seeds with soil, a tank mixture of the safener to be tested, viz. n-butyl 2-(5-chloro-8-quinolinoxy)acetate (compound 125) or 2-phenoxyethyl 2-(5-chloro-8-quinolinoxy)acetate (compound 188), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 20.

TABLE 20

| Safener Compound No. | Safener g a.i./ha | Herbicide g a.i./ha | Relative protective action in % |
|---|---|---|---|
| 125 | 400 | 400 | 65 |
| | 200 | 400 | 65 |
| | 100 | 400 | 45 |
| | 200 | 200 | 55 |
| | 100 | 200 | 55 |
| | 50 | 200 | 55 |
| 188 | 400 | 400 | 60 |
| | 200 | 400 | 70 |
| | 100 | 400 | 70 |
| | 200 | 200 | 55 |
| | 100 | 200 | 50 |
| | 50 | 200 | 45 |

Example 55: Postemergence test with safener and herbicide as tank mixture

Wheat seeds of the "Besso" variety are sown in a greenhouse in plastic pots (diameter at the top 11 cm) containing 0.5 l of sandy loam. A tank mixture of the safener to be tested, viz. 1-methylhexyl 2-(5-chloro-8-quinolinoxy)acetate (compound 357), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 21.

TABLE 21

| Safener g a.i./ha | Herbicide g a.i./ha | Relative protective action in % |
|---|---|---|
| 200 | 200 | 65 |
| 100 | 200 | 80 |
| 100 | 100 | 75 |
| 50 | 100 | 75 |

Example 56: Postemergence test with safener and herbicide as tank mixture

Wheat seeds of the "Besso" variety are sown in a greenhouse in plastic pots (diameter at the top 11 cm) containing 0.5 l of sandy loam. A tank mixture of the safener to be tested, viz. 1-methylhexyl 2-(5-chloro-8-quinolinoxy)acetate (compound 357), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 10 days after application. The plants treated with the herbicide alone as well as the completely untreated controls serve as reference for the evaluation. The results are reported in Table 22.

TABLE 22

| Safener g a.i./ha | Herbicide g a.i./ha | Relative protective action in % |
|---|---|---|
| 200 | 400 | 40 |
| 100 | 200 | 70 |
| 50 | 100 | 55 |

Example 57: Postemergence test with safener and herbicide as tank mixture

Barley seeds of the "Cornel" variety are sown in a greenhouse in plastic pots (diameter at the top 11 cm) containing 0.5 l of sandy loam. A tank mixture of the safener to be tested, viz. 1-methylhexyl 2-(5-chloro-8-quinolinoxy)acetate (compound 357), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 21 days after application. The plants treated with the herbicide alone as well as the completely untreated controls serve as reference for the evaluation. The results are reported in Table 23.

TABLE 23

| Safener g a.i./ha | Herbicide g a.i./ha | Relative protective action in % |
|---|---|---|
| 200 | 200 | 55 |
| 100 | 200 | 65 |
| 100 | 100 | 60 |
| 50 | 100 | 60 |

Example 58: Postemergence test with safener and herbicide as tank mixture

Barley seeds of the "Cornel" variety are sown in a greenhouse in plastic pots (diameter at the top 11 cm) containing 0.5 l of sandy loam. A tank mixture of the safener to be tested, viz. 1-methylhexyl 2-(5-chloro-8-quinolinoxy)acetate (compound 357), together with the herbicide, viz. 2-[4,5-dihydro-5-methyl-5-(1-methylethyl)-4-oxo-1H-imidazol-2-yl]-5-ethyl nicotinic acid, in different ratios is applied in postemergence process (three leaf stage of the plant). Percentage evaluation of the protective action is made 10 days after application. The plants treated with the herbicide alone as well as the completely untreated controls serve as reference for the evaluation. The results are reported in Table 24.

TABLE 24

| Safener g a.i./ha | Herbicide g a.i./ha | Relative protective action in % |
|---|---|---|
| 200 | 400 | 30 |
| 100 | 200 | 40 |
| 50 | 100 | 30 |

What is claimed is:

1. A composition comprising a herbicidally-effective amount of a herbicide of formula II

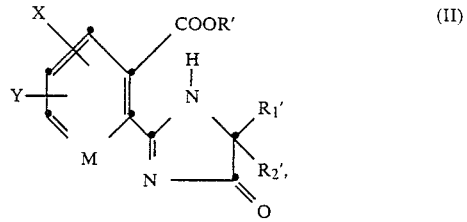

wherein R' is hydrogen, $C_1$–$C_4$alkyl, the ammonium cation or an organic ammonium cation, $R_1'$ is $C_1$–$C_4$alkyl, $R_2'$ is $C_1$–$C_4$alkyl or $C_3$–$C_6$cycloalkyl, or $R_1'$ and $R_2'$ together are $C_4$alkylene or $C_5$alkylene, M is the structural unit =CH— or =N—, X and Y are each independently of the other hydrogen, $C_1$–$C_4$alkyl or halogen or, if m is =N—, are additionally the structural unit —C(X$_1$)=C(X$_2$)—C(X$_3$)=C(X$_4$)—, wherein X$_1$, X$_2$, X$_3$ and X$_4$ are hydrogen or one or two of X$_1$, X$_2$, X$_3$ and X$_4$ are C$_1$–C$_4$alkyl and the others are hydrogen, and a non-phytotoxic antidotally-effective amount of a compound of formula I

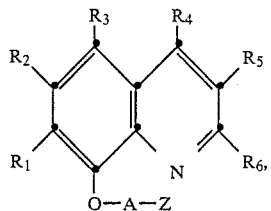
(I)

wherein
R$_1$ is hydrogen, chlorine, bromine or iodine, R$_2$ is hydrogen, R$_3$ is hydrogen, chlorine, bromine or nitro, R$_4$ and R$_5$ are hydrogen and R$_6$ is hydrogen or methyl, A is a group selected from —CH$_2$—, —CH$_2$CH$_2$— or —CH(CH$_3$)—, and Z is cyano

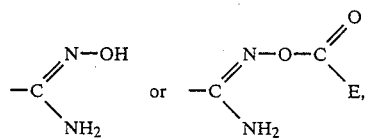

—COOR$_{12}$, —COSR$_{13}$ or —CONR$_{14}$R$_{15}$, wherein

E is —R$_7$, —OR$_8$, —SR$_9$ or —NR$_{10}$R$_{11}$, and

R$_7$ is C$_1$–C$_4$alkyl which is unsubstituted or mono- or disubstituted by chlorine or bromine, or is monosubstituted by C$_1$–C$_4$alkoxy, or is cyclopropyl, C$_2$–C$_3$alkenyl, phenyl or phenyl which is monosubstituted by chlorine, or is benzyl, or is furanyl or furanyl which is monosubstituted by bromine, or is tetrahydrofuranyl or dichloropyrimidine, R$_8$ is C$_1$–C$_4$alkyl which is unsubstituted or monosubstituted by bromine, or is allyl, phenyl or benzyl, R$_9$ is C$_1$–C$_5$alkyl, R$_{10}$ is C$_1$–C$_4$alkyl, phenyl or phenyl which is mono- or disubstituted by chlorine or monosubstituted by trifluoromethyl, and R$_{11}$ is hydrogen or methoxy, R$_{12}$ is hydrogen, an alkali metal cation, the ammonium cation or an ammonium cation which is trisubstituted by C$_1$–C$_4$alkyl or mono-hydroxy-C$_1$–C$_4$alkyl, or is C$_1$–C$_{12}$alkyl, or is C$_1$–C$_4$alkyl which is monosubstituted by halogen, C$_1$–C$_3$alkoxy, phenoxy, phenyl or tetrahydrofuranyl, or is C$_2$–C$_4$alkenyl or C$_3$–C$_4$alkynyl, or is cyclohexyl, phenyl or phenyl which is mon- or disubstituted by methyl, R$_{13}$ is C$_5$–C$_{10}$-alkyl, R$_{14}$ is hydrogen, C$_1$–C$_4$alkyl or C$_1$–C$_4$alkyl which is monosubstituted by hydroxy, C$_1$–C$_4$alkoxy, di(C$_1$–C$_4$alkyl)amino, (monohydroxy-C$_1$–C$_4$alkyl)amino, di(monohydroxy-C$_1$–C$_4$alkyl)amino, phenyl, tetrahydrofuranyl, piperidinyl or morpholinyl, or is allyl, cyclohexyl or amino, and R$_{15}$ is hydrogen, C$_1$–C$_4$alkyl or monohydroxy-C$_1$–C$_4$alkyl, or wherein —NR$_{14}$R$_{15}$ form the morpholino ring, or wherein A and Z together are tetrahydrofuran-2-one.

2. A method of protecting cultivated plants from the harmful effects of a herbicide of formula II

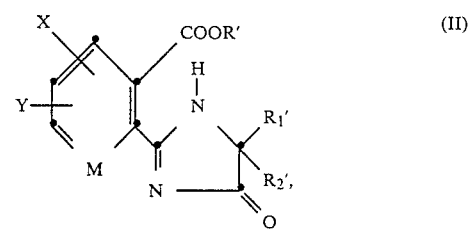
(II)

wherein R' is hydrogen, C$_1$–C$_4$alkyl, the ammonium cation or an organic ammonium cation, R$_1$' is C$_1$–C$_4$alkyl, R$_2$' is C$_1$–C$_4$alkyl or C$_3$–C$_6$cycloalkyl, or R$_1$' and R$_2$' together are C$_4$alkylene or C$_5$alkylene, M is the structural unit =CH— or =N—, X and Y are each independently of the other hydrogen, C$_1$–C$_4$alkyl or halogen or, if m is =N—, are additionally the structural unit —C(X$_1$)=C(X$_2$)—C(X$_3$)=C(X$_4$)—, wherein X$_1$, X$_2$, X$_3$ and X$_4$ are hydrogen or one or two of X$_1$, X$_2$, X$_3$ and X$_4$ are C$_1$–C$_4$alkyl and the others are hydrogen, which process comprises treating said cultivated plants, parts thereof or areas of soil intended for the cultivation of said plants with a safening amount of a compound of formula I

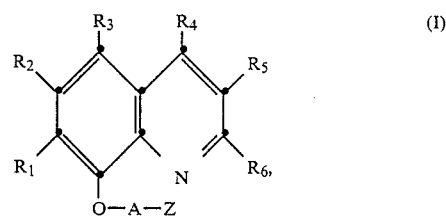
(I)

wherein
R$_1$ is hydrogen, chlorine, bromine or iodine, R$_2$ is hydrogen, R$_3$ is hydrogen, chlorine, bromine or nitro, R$_4$ and R$_5$ are hydrogen and R$_6$ is hydrogen or methyl, A is a group selected from —CH$_2$—, —CH$_2$CH$_2$— or —CH(CH$_3$)—, and Z is cyano

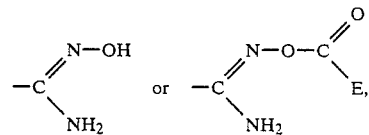

—COOR$_{12}$, —COSR$_{13}$ or —CONR$_{14}$R$_{15}$, wherein

E is —R$_7$, —OR$_8$, —SR$_9$ or —NR$_{10}$R$_{11}$, and

R$_7$ is C$_1$–C$_4$alkyl which is unsubstituted or mono- or disubstituted by chlorine or bromine, or is monosubstituted by C$_1$–C$_4$alkoxy, or is cyclopropyl, C$_2$–C$_3$alkenyl, phenyl or phenyl which is monosubstituted by chlorine, or is benzyl, or is furanyl or furanyl which is monosubstituted by bromine, or is tetrahydrofuranyl or dichloropyrimidine, R$_8$ is C$_1$–C$_4$alkyl which is unsubstituted or monosubstituted by bromine, or is allyl, phenyl or benzyl, R$_9$ is C$_1$C$_5$alkyl, R$_{10}$ is C$_1$–C$_4$alkyl, phenyl or phenyl which is mono- or disubstituted by chlorine or monosubstituted by trifluoromethyl, and R$_{11}$ is hydrogen or methoxy, R$_{12}$ is hydrogen, an alkali metal cation, the ammonium cation or an ammonium cation which is trisubstituted by C$_1$–C$_4$alkyl or mono-hydroxy-C$_1$–C$_4$alkyl, or is $C_1$–$C_{12}$alkyl, or is $C_1$–$C_4$alkyl which is monosubstituted by halogen, $C_1$–$C_3$alkoxy, phenoxy, phenyl or tetrahydrofuranyl, or is $C_2$–$C_4$alkenyl or $C_3$–$C_4$alkynyl, or is cyclohexyl, phenyl or phenyl which is mon- or disubstituted by methyl, $R_{13}$ is $C_5$–$C_{10}$alkyl, $R_{14}$ is hydrogen, $C_1$–$C_4$alkyl or $C_1$–$C_4$alkyl which is monosubstituted by hydroxy, $C_1$–$C_4$alkoxy, di($C_1$–$C_4$alkyl)amino, (monohydroxy-$C_1$–$C_4$alkyl)amino, di(-monohydroxy-$C_1$–$C_4$alkyl)amino, phenyl, tetrahydrofuranyl, piperidinyl or morpholinyl, or is allyl, cyclohexyl or amino, and $R_{15}$ is hydrogen, $C_1$–$C_4$alkyl or monohydroxy-$C_1$–$C_4$alkyl, or wherein —$NR_{14}R_{15}$ form the morpholino ring, or wherein A and Z together are tetrahydrofuran-2-one.

3. A method according to claim 2 which comprises the use of a compound of formula I, wherein Z is —$COOR_{12}$, wherein $R_{12}$ is hydrogen, an alkali metal cation, the ammonium cation or an ammonium cation which is trisubstituted by $C_1$–$C_4$alkyl or monohydroxy-$C_1$–$C_4$alkyl, or is $C_1$–$C_{12}$alkyl, or is $C_1$–$C_4$alkyl which is monosubstituted by halogen, $C_1$–$C_3$alkoxy, phenoxy, phenyl or tetrahydrofuranyl, or is $C_2$–$C_4$alkenyl or $C_3$–$C_4$alkynyl, or is cyclohexyl, phenyl or phenyl which is mono- or disubstituted by methyl.

4. A method according to claim 2 which comprises the use of a compound of formula I, wherein Z is —$COSR_{13}$, in which $R_{13}$ is $C_5$–$C_{10}$alkyl.

5. A method according to claim 2 which comprises the use of a compound of formula I, wherein $R_1$, $R_2$, $R_4$, $R_5$ and $R_6$ are hydrogen, $R_3$ is hydrogen or chlorine, A is the —$CH_2$— group and Z is cyano, the

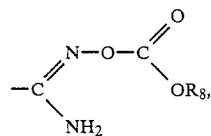

or —$COOR_{12}$ group, in which $R_8$ is $C_1$–$C_4$alkyl and $R_{12}$ is $C_1$–$C_8$alkyl or $C_2$–$C_4$alkenyl.

6. A method according to claim 5 which comprises the use of a compound of formula I, wherein $R_8$ is methyl.

7. A method according to claim 5 which comprises the use of a compound of formula I, wherein $R_{12}$ is n-butyl, 1-methylhexyl or methylallyl.

8. A method according to claim 2 which comprises the use of 5-chloro-8-(cyanomethoxy)quinoline.

9. A method according to claim 2 which comprises the use of 0-(methoxycarbony)-2-(quinolinoxy)acetamidoxime.

10. A method according to claim 2 which comprises the use of n-butyl 2-(5-chloro-8-quinolinoxy)acetate.

11. A method according to claim 2 which comprises the use of methylallyl 2-(5-chloro-8-quinolinoxy)acetate.

12. A method according to claim 2 which comprises the use of 1-methylhexyl 2-(5-chloro-8-quinolinoxy)acetate.

13. A method according to claim 2 which comprises protecting cultivated plants from the harmful effects of herbicides of formula II, wherein R' is hydrogen, methyl, the ammonium cation or an organic ammonium cation, $R_1'$ is methyl, $R_2'$ is isopropyl, and M, X and Y are as defined for formula II.

14. A method according to claim 13, wherein R' is methyl, $R_1'$ is methyl, $R_2'$ is isopropyl, M is the structural unit =CH—, X is hydrogen and Y is 4- or 5-methyl.

15. A method according to claim 2 which comprises protecting cultivated plants from the harmful effects of 2-[4,5-dihydro-5-methyl-5-(1-methylethyl)-4-oxo-1H-imidazol-2-yl]-5-ethyl nicotinic acid.

16. A method according to claim 2 which comprises protecting cultivated plants from the harmful effects of 2-[4,5-dihydro-5-methyl-5-(1-methylethyl)-4-oxo-1H-imidazol-2-yl]-3-quinolinecarboxylic acid.

17. A method according to claim 2 wherein the crops to be protected are cereals.

18. A method according to claim 17 wherein the crops to be protected are wheat, barley and maize.

19. A method according to claim 2 which comprises treating crops of cultivated plants or areas for growing said plants with 0.1 to 10 kg/ha of a compound of formula I as claimed in claim 1.

20. A method according to claim 19 which comprises treating crops of cultivated plants or areas for growing said plants with 0.5 to 2 kg/ha of a compound of formula I as claimed in claim 1.

21. A method according to claim 2 which comprises treating seeds of cultivated plants with a compound of formula I as claimed in claim 1.

22. A method according to claim 21 which comprises treating seeds of cultivated plants with 0.01 to 10 g/kg of seeds with a compound of formula I as claimed in claim 2.

23. A method according to claim 22 which comprises treating seeds of cultivated plants with 0.05 to 1 g/kg of seeds of a compound of formula I as claimed in claim 2.

24. A method according to claim 2 which comprises protecting cultivated plants from the harmful effects of 2-[4,5-dihydro-5-methyl-5-(1-methylethyl)-4-oxo-1H-imidazol-2-yl]nicotinic acid, 2-[4,5-dihydro-5-methyl-5-(1-methylethyl)-4-oxo-1H-imidazol-2-yl]-5-ethyl nicotinic acid or 2-[4,5-dihydro-5-methyl-5-(1-methylethyl)-4-oxo-1H-imidazol-2-yl]-3-quinolinecarboxylic acid, by treating the seeds of said plants with 5-chloro-8-(cyanomethoxy)quinoline, 0-methoxycarbonyl)-2-(8-quinolinoxy)acetamidoxime, n-butyl 2-(5-chloro-8-quinolinoxy)acetate or methylallyl 2-(5-chloro-8-quinolinoxy)acetate.

25. A method according to claim 2 which comprises protecting cultivated plants from the harmful effects of 2-[4,5-dihydro-5-methyl-5-(1-methylethyl)-4-oxo-1H-imidazol-2-yl]-5-ethyl nicotinic acid or 2-[4,5-dihydro-5-methyl-5-(1-methylethyl)-4-oxo-1H-imidazol-2-yl]-3-quinolinecarboxylic acid, by treating the seeds of said plants with 5-chloro-8-(cyanomethoxy)quinoline, 0-methoxycarbonyl)-2-(8-quinolinoxy)acetamidoxime, n-butyl 2-(5-chloro-8-quinolinoxy)acetate, methylallyl 2-(5-chloro-8-quinolinoxy)acetate, or 1-methylhexyl-2-(5-chloro-8-quinolinoxy)acetate.

26. A method according to claim 23 wherein the crops to be protected are crops of cereals.

* * * * *